United States Patent [19]

Wang

[11] 4,148,788
[45] Apr. 10, 1979

[54] SYNTHESIS OF THYMOSIN $\alpha_1$

[75] Inventor: Su-Sun Wang, Bloomfield, N.J.

[73] Assignee: Hoffmann-La Roche Inc., Nutley, N.J.

[21] Appl. No.: 917,059

[22] Filed: Jun. 19, 1978

Related U.S. Application Data

[63] Continuation-in-part of Ser. No. 871,563, Jan. 23, 1978, which is a continuation-in-part of Ser. No. 789,898, Apr. 22, 1977, abandoned.

[51] Int. Cl.² .................... C07C 103/52; A61K 37/00
[52] U.S. Cl. .............................. 260/112.5 R; 424/177
[58] Field of Search .................. 260/112.5 R; 424/177

[56] References Cited

U.S. PATENT DOCUMENTS

| 4,002,740 | 1/1977 | Goldstein et al. | 424/177 |
| 4,010,148 | 3/1977 | Goldstein | 260/112.5 R |
| 4,082,737 | 4/1978 | McGregor | 260/112.5 R |

Primary Examiner—Delbert R. Phillips
Attorney, Agent, or Firm—Jon S. Saxe; George M. Gould

[57] ABSTRACT

Thymosin $\alpha_1$, was chemically synthesized by the fragment condensation of the protected amino terminal tetradecapeptide with the protected carboxyl terminal tetradecapeptide and by solid phase peptide synthesis. Thymosin $\alpha_1$ is active as an agent which affects regulation, differentiation and function of thymus dependent lymphocytes (T cells).

10 Claims, No Drawings

SYNTHESIS OF THYMOSIN α₁

RELATED APPLICATIONS

This application is a continuation-in-part of copending application Ser. No. 871,563, filed Jan. 23, 1978 which in turn is a continuation-in-part of Ser. No. 789,898 filed Apr. 22, 1977, now abandoned.

BACKGROUND OF THE INVENTION

Several polypeptide factors present in the thymus gland have been implicated to play important roles in the development and maintenance of immunological competence in man and in animals. The importance of the immune system in the defense against cancer and tumor cells is now widely recognized. In recent years, a few polypeptides shown to be able to stimulate maturation, differentiation and function of T cells have been isolated from bovine thymus. Among them, the acidic peptide thymosin $\alpha_1$, has been intensively studied. Its structure and activity have been described in U.S. Pat. No. 4,079,127. Additionally, it should be noted that in the parent case thereof, U.S. patent application Ser. No. 736,638 filed Oct. 28, 1976, the structure of thymosin $\alpha_1$, was erroneously given as that of [Asn²]-thymosin $\alpha_1$.

The correct structure of thymosin $\alpha_1$ is as follows:

Ac-Ser-Asp-Ala-Ala-Val-Asp-Thr-Ser-Ser-Glu-Ile-
Thr-Thr-Lys-Asp-Leu-Lys-Glu-Lys-Lys-Glu-
Val-Val-Glu-Glu-Ala-Glu-Asn-OH

DESCRIPTION OF THE INVENTION

Thymosin $\alpha_1$ has been chemically synthesized in a preferred embodiment by the condensation of the novel protected carboxyl terminal tetradecapeptide of the sequence TFA .
H-Asp(OBzl)-Leu-Lys(Z)-Glu(OBzl)-Lys(Z)-
Lys(Z)-Glu(OBzl)-Val-Val-Glu(OBzl)-
Glu(OBzl)-Ala-Glu(OBzl)-Asn-OBzl    I with the novel protected amino terminal tetradecapeptide of the sequence Ac-Ser(Bzl)-Asp(OBzl)-Ala-Ala-Val-Asp(OBzl)-
Thr(Bzl)-Ser(Bzl)-Ser(Bzl)-Glu-Ile-Thr(Bzl)-
Thr(Bzl)-Lys(Z)-OH    II followed by removal of the protecting groups.

The aforesaid coupling reaction can be carried out utilizing procedures well known in solution phase peptide synthesis. Thus, for example, the amino terminal tetradecapeptide can be activated with a carbodiimide coupling agent such as dicyclohexylcarbodiimide (DCC) and 1-hydroxybenzotriazole (HOBT) and the ensuing active ester is reacted with the trifluoroacetic acid (TFA) salt of the carboxyl terminal tetradecapeptide to yield the desired thymosin $\alpha_1$ in protected form of the following structure:

Ac-Ser(Bzl)-Asp(OBzl)-Ala-Ala-Val-Asp(OBzl)-
Thr(Bzl)-Ser(Bzl)-Ser(Bzl)-Glu(OBzl)-Ile-
Thr(Bzl)-Thr(Bzl)-Lys(Z)-Asp(Bzl)-Leu-Lys(Z)-
Glu(OBzl)-Lys(Z)-Lys(Z)-Glu(OBzl)-Val-Val-
Glu(OBzl)-Glu(OBzl)-Ala-Glu(OBzl)-Asn-OBzl    III

Removal of the protecting groups from the above compound is readily accomplished by procedures known per se, such as, for example, by treatment with anhydrous acid (HF) preferably in the presence of anisole.

The strategy employed in the chemical synthesis of the protected carboxyl terminal tetradecapeptide I was as follows:

For the synthesis of the carboxyl terminal tripeptide Boc-Ala-Glu(OBzl)-Asn-OBzl, H-Glu(OBzl)-OH was first coupled to Boc-Ala-OSu to give the protected dipeptide fragment Boc-Ala-Glu(OBzl)-OH which was then condensed with HCl . H-Asn-OBzl via the DCC/HOSu procedure of Wunsch and Drees, Chem. Ber. 99, 110 (1966). The hydrochloride salt of asparagine benzyl ester was prepared from Boc-Asn-OBzl which in turn was synthesized from commercially available Boc-Asn-OH and benzyl bromide using the cesium salt of the amino acid. The Boc-protecting group was removed by a 30 minute treatment with 4 N HCl in dry THF.

Reaction between H-Glu(OBzl)-OH and Boc-Glu(OBzl)-OSu produced Boc-Glu(OBzl)-Glu(OBzl)-OH as a colorless clear oil. It was subsequently utilized in the synthesis of the pentapeptide Boc-Glu(OBzl)-Glu(OBzl)-Ala-Glu(OBzl)-Asn-OBzl in a DCC/HOSu mediated fragment condensation using HCl . H-Ala-Glu(OBzl)-Asn-OBzl that was derived from Boc-Ala-Glu(OBzl)-Asn-OBzl upon 4 N HCl/THF treatment. The aforesaid protected pentapeptide was obtained in good yield as a crystalline pure material.

For the preparation of the octapeptide Boc-Glu(OBzl)-Val-Val-Glu(OBzl)-Glu(OBzl)-Ala-Glu(OBzl)-Asn-OBzl, the required tripeptide Boc-Glu(OBzl)-Val-Val-OH was first prepared. Boc-Val-OSu was allowed to react with free valine to provide Boc-Val-Val-OH which on deblocking with 4 N HCl in THF followed by reaction with Boc-Glu(OBzl)-OSu yielded the desired tripeptide which was crystallized as cyclohexylamine salt Boc-Glu(OBzl)-Val-Val-OH . CHA. The cyclohexylamine salt was converted to the free acid and was then coupled by DCC in the presence of HOSu to HCl . H-Glu(OBzl)-Glu(OBzl)-Ala-Glu(OBzl)-Asn-OBzl that was derived from Boc-Glu(OBzl)-Glu(OBzl)-Ala-Glu(OBzl)-Asn-OBzl on treatment with HCl in THF. The protected octapeptide Boc-Glu(OBzl)-Val-Val-Glu(OBzl)-Glu(OBzl)-Ala-Glu(OBzl)-Asn-OBzl was obtained in purified form as an amorphous solid.

For the synthesis of the undecapeptide Boc-Glu(OBzl)-Lys(Z)-Lys(Z)-Glu(OBzl)-Val-Val-Glu(OBzl)-Glu(OBzl)-Ala-Glu(OBzl)-Asn-OBzl, the required tripeptide fragment was synthesized starting from Boc-Lys(Z)-OSu and H-Lys(Z)-OH. The dipeptide Boc-Lys(Z)-Lys(Z)-OH thus obtained was treated with 4 N HCl in THF and the ensuing salt HCl . H-Lys(Z)-Lys(Z)-OH was then allowed to react with Boc-Glu(OBzl)-OSu to provide the desired tripeptide Boc-Glu(OBzl)-Lys(Z)-Lys(Z)-OH. The tripeptide was then activated with DCC and HOSu according to the procedure of Weygard et al, Z. Naturforsch, 21b, 426 (1966) and the solution of the tripeptide active ester Boc-Glu(OBzl)-Lys(Z)-Lys(Z)-OSu generated in situ was combined with the trifluoroacetate salt of H-Glu(OBzl)-Val-Val-Glu(OBzl)-Glu(OBzl)-Ala-Glu(OBzl)-Asn-OBzl derived from the corresponding blocked octapeptide by a 30 minute treatment with TFA. The desired protected undecapeptide Boc-Glu(OBzl)-Lys(Z)-Lys(Z)-Glu-(OBzl)-Val-Val-Glu(OBzl)-Glu(OBzl)-Ala-Glu(OBzl)-Asn-OBzl was thus obtained. Amino acid analysis and microanalysis gave the expected values.

The synthesis of the protected tetradecapeptide followed a similar pattern. Boc-Leu-OSu was coupled to H-Lys(Z)-OH to provide Boc-Leu-Lys(Z)-OH. After removal of the $N^\alpha$-Boc-group with 4 N HCl in THF and reaction with Boc-Asp(OBzl)-OSu the protected tripeptide Boc-Asp(OBzl)-Leu-Lys(Z)-OH was obtained as a crystalline pure solid. It was converted into the active ester Boc-Asp(OBzl)-Leu-Lys(Z)-OSu and condensed with the trifluoroacetate salt of H-Glu(OBzl)-Lys(Z)-Lys(Z)-Glu(OBzl)-Val-Val-Glu(OBzl)-Glu(OBzl)-Ala-Glu(OBzl)-Asn-OBzl obtained from TFA treatment of the corresponding blocked undecapeptide. The desired product Boc-Asp(OBzl)-Leu-Lys(Z)-Glu(OBzl)-Lys(Z)-Lys(Z)-Glu(OBzl)-Val-Val-Glu(OBzl)-Glu(OBzl)-Ala-Glu(OBzl)-Asn-OBzl was obtained in good yield. Thin layer chromatography indicated that the product was homogeneous.

The protected amino terminal tetradecapeptide Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(Z)-OH was assembled using procedures well known in the peptide synthesis art from an acetyl tetrapeptide fragment, a hexapeptide, and another tetradecapeptide. For the synthesis of the amino terminal acetyl tetrapeptide, Ac-Ser(Bzl)-OBzl was prepared from Ac-OSu and the hydrochloride salt of H-Ser(Bzl)-OBzl. The same compound can also be prepared from Ac-Ser(Bzl)-OH and benzyl bromide via the cesium salt of the amino acid. Hydrazinolysis of Ac-Ser(Bzl)-OBzl gave Ac-Ser(Bzl)-HNNH$_2$ as a pure crystalline solid in good yield. Deblocking of Boc-Ala-Ala-OH afforded the dipeptide hydrochloride salt HCl . H-Ala-Ala-OH. Coupling of this dipeptide with Boc-Asp(OBzl)-OSu provided the tripeptide Boc-Asp(OBzl)-Ala-Ala-OH which was isolated as the dicyclohexyl amine salt. Removal of the amino protecting group and condensation with Ac-Ser(Bzl)-HNNH$_2$ via the azide procedure of Honzl and Rudinger, Collection Czech. Chem. Commun. 26, 2333 (1961) gave the partially protected tetrapeptide Ac-Ser(Bzl)-Asp(OBzl)-Ala-Ala-OH which on reaction with equivalent amounts of hydrazine mediated by the dicyclohexylcarbodiimide in the presence of 1-hydroxybenzotriazole produced the desired intermediate Ac-Ser(Bzl)-Asp(OBzl)-Ala-Ala-HNNH$_2$.

For the synthesis of the hexapeptide Boc-Val-Asp(OBzl)-Thr(Bzl)-Ser(Bzl)-Ser(Bzl)-Glu(OBzl)-HNNH$_2$, a process involving the stepwise elongation of the peptide chain from the C-terminal end was adopted. Thus, H-Glu(OBzl)-OH was coupled with Boc-Ser(Bzl)-OSu to form the protected dipeptide Boc-Ser(Bzl)-Glu(OBzl)-OH which on removal of the Boc-group and further reaction with Boc-Ser(Bzl)-OSu gave rise to the tripeptide Boc-Ser(Bzl)-Ser(Bzl)-Glu(OBzl)-OH. Deprotection of the amino group followed by condensation of the resultant tripeptide salt HCl.H-Ser(Bzl)-Ser(Bzl)-Glu(OBzl)-OH with Boc-Thr(Bzl)-OSu yielded the protected tetrapeptide Boc-Thr(Bzl)-Ser(Bzl)-Ser(Bzl)-Glu(OBzl)-OH which on treatment with HCl in THF removed the Boc-group and further reaction with Boc-Asp(OBzl)-OSu resulted in the formation of the protected pentapeptide Boc-Asp(OBzl)-Thr(Bzl)-Ser(Bzl)-Ser(Bzl)-Glu(OBzl)-OH. The Boc-group on this compound was similarly recovered with HCl treatment and the ensuing product HCl . H-Asp(OBzl)-Thr(Bzl)-Ser(Bzl)-Ser(Bzl)-Glu(OBzl)-OH was subsequently coupled to Boc-Val-OSu to give Boc-Val-Asp(OBzl)-Thr(Bzl)-Ser(Bzl)-Ser(Bzl)-Glu(OBzl)-OH as a crystalline pure material.

The $\alpha$-carboxyl group on the terminal glutamic acid residue of the aforesaid hexapeptide was then specifically converted into the hydrazide function by the reaction with an equivalent amount of hydrazine using dicyclohexylcarbodiimide as coupling agent in the presence of 1-hydroxybenzotriazole. The desired hexapeptide hydrazide Boc-Val-Asp(OBzl)-Thr(Bzl)-Ser(Bzl)-Ser(Bzl)-Glu(OBzl)-HNNH$_2$ was isolated as pure crystalline solid in a reasonable yield.

For the synthesis of the protected tetrapeptide Boc-Ile-Thr(Bzl)-Thr(Bzl)-Lys(Z)-OH, a similar stepwise procedure using the N-hydroxysuccinimide active ester procedure of Anderson et al, J. Amer. Chem. Soc. 86, 1839 (1964) was utilized. Reaction between Boc-Thr(Bzl)-OSu and H-Lys(Z)-OH gave the dipeptide Boc-Thr(Bzl)-Lys(Z)-OH as an oil which was deprotected at the $\alpha$-amino end and allowed to react with Boc-Thr(Bzl)-OSu to provide the tripeptide Boc-Thr(Bzl)-Thr(Bzl)-Lys(Z)-OH as a crystalline solid. Removal of the Boc-group and reaction of the resultant material HCl.H-Thr(Bzl)-Thr(Bzl)-Lys(Z)-OH with Boc-Ile-OSu yielded the desired protected tetrapeptide Boc-Ile-Thr(Bzl)-Thr(Bzl)-Lys(Z)-OH as a crystalline pure compound after chromatography on a silica gel column. This tetrapeptide fragment was then deprotected at the amino terminal and condensed with the hexapeptide Boc-Val-Asp(OBzl)-Thr(Bzl)-Ser(Bzl)-Ser(Bzl)-Glu(OBzl)-HNNH$_2$ by the azide method to produce the protected decapeptide Boc-Val-Asp(OBzl)-Thr(Bzl)-Ser(Bzl)-Ser(Bzl)-Glu(OBzl)-Ile-Thr(Bzl)-Thr(Bzl)-Lys(Z)-OH in good yield.

Removal of the Boc-group from the decapeptide compound with TFA and subsequent coupling with the N-terminal tetrapeptide Ac-Ser(Bzl)-Asp(OBzl)-Ala-Ala-HNNH$_2$ through the azide procedure resulted in formation of the required protected tetradecapeptide Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(Z)-OH. For the final coupling, This acetyl tetradecapeptide was activated with DCC and HOBT and the ensuing active ester was then allowed to react with TFA . H-Asp(OBzl)-Leu-Lys(Z)-Glu(OBzl)-Lys(Z)-Lys(Z)-Glu(OBzl)-Val-Val-Glu(OBzl)-Glu(OBzl)-Ala-Glu(OBzl)-Asn-OBzl which was derived from the corresponding blocked compound on treatment with TFA to give the protected acetyl octacosapeptide Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(Z)-Asp(OBzl)-Leu-Lys(Z)-Glu(OBzl)-Lys(Z)-Lys(Z)-Glu(OBzl)-Val-Val-Glu(OBzl)-Glu(OBzl)-Ala-Glu(OBzl)-Asn-OBzl. Treatment with anhydrous HF removed all the protecting groups and purification on ion-exchange chromatography yielded thymosin $\alpha_1$.

[The synthesis of [Asn$^2$]-thymosin$\alpha_1$ followed the same pattern as the synthesis of thymosin$\alpha_1$. All of the intermediates used were the same except the N-terminal acetyl tetrapeptide hydrazide Ac-Ser(Bzl)-Asn-Ala-Ala-HNNH$_2$. For the synthesis of this compound, Boc-Ala-Ala-OH was first converted into Boc-Ala-Ala-OBzl which on selective removal of the Boc-group with HCl gave the dipeptide ester salt HCl.H-Ala-Ala-OBzl. The dipeptide was then coupled with Boc-Asn-OH using the DCC-HOBT procedure of Konig and Geiger, Chem. Ber. 103, 788 (1970) to give the protected tripeptide ester Boc-Asn-Ala-Ala-OBzl which was treated with HCl in THF to remove the Boc-group. The resultant product HCl.H-Asn-Ala-Ala-OBzl was then condensed (DCC-HOBT procedure) with Ac-Ser(Bzl)-OH.DCHA to afford the desired tetrapeptide Ac-Ser(Bzl)-Asn-Ala-Ala-OBzl.

The corresponding hydrazide Ac-Ser(Bzl)-Asn-Ala-Ala-HNNH$_2$ was obtained in good yield on hydrazinolysis of this compound. Fragment condensation between the hydrazide and the decapeptide TFA.H-Val-Asp(OBzl)-Thr(Bzl)-Ser(Bzl)-Ser(Bzl)-Glu(OBzl)-Ile-Thr(Bzl)-Thr(Bzl)-Lys(Z)-OH produced the protected tetradecapeptide Ac-Ser(Bzl)-Asn-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(Z)-OH. This compound was then coupled to the deblocked C-terminal tetradecapeptide TFA salt discussed above to give the corresponding protected [Asn$^2$]-thymosin$\alpha_1$. Removal of all the protecting groups by treatment with anhydrous HF followed by column chromatography purification gave the desired analog [Asn$^2$]-thymosin$\alpha_1$.]

In a further aspect of this invention it has been found that several of the intermediate peptides used in the above synthesis of thymosin$\alpha_1$[and[Asn$^2$]-thymosin$\alpha_1$] have activity in the regulation, differentiation and function of T-cells.

Thus, the protected octapeptide Boc-Glu(OBzl)-Val-Val-Glu(OBzl)-Glu(OBzl)-Ala-Glu(OBzl)-Asn-OBzl can be deprotected by hydrogenolysis followed by treatment with trifluoroacetic acid in the usual manner to give the free octapeptide Glu-Val-Val-Glu-Glu-Ala-Glu-Asn. This product is purified by ion-exchange column chromatography to yield material homogeneous on thin layer chromatography and paper electrophoresis.

Similarly, deprotection of the protected undecapeptide Boc-Glu(OBzl)-Lys(Z)-Lys(Z)-Glu(OBzl)-Val-Val-Glu(OBzl)-Glu(OBzl)-Ala-Glu(OBzl)-Asn-OBzl with anhydrous hydrofluoric acid provided the free undecapeptide Glu-Lys-Lys-Glu-Val-Val-Glu-Glu-Ala-Glu-Asn which was homogeneous on paper electrophorisis after ion-exchange column chromatography.

The carboxy terminal tetradecapeptide Asp-Leu-Lys-Glu-Lys-Lys-Glu-Val-Val-Glu-Glu-Ala-Glu-Asn was obtained in like manner from the protected tetradecapeptide Boc-Asp(OBzl)-Leu-Lyz(Z)-Glu(OBzl)-Lys(Z)-Lys(Z)-Glu(OBzl)-Val-Val-Glu(OBzl)-Glu(OBzl)-Ala-Glu(OBzl)-Asn-OBzl by anhydrous hydrofluoric acid treatment and purification on an ion exchange column.

The amino terminal tetradecapeptide Ac-Ser-Asp-Ala-Ala-Val-Asp-Thr-Ser-Ser-Glu-Ile-Thr-Thr-Lys-OH was obtained in like manner from the protected tetradecapeptide. Ac-Ser(Bzl)-Asp(OBzl)-Ala-Ala-Val-Asp(OBzl)-Thr(Bzl)-Ser(Bzl)-Ser(Bzl)-Glu-Ile-Thr(Bzl)-Thr(Bzl)-Lys(Z)-OH by anhydrous hydrofluoric acid treatment and purification on an ion exchange column.

Thymosin$\alpha_1$, [[Asn$^2$]-thymosin$\alpha_1$,] or the aforesaid novel octa-, undeca- or tetradecapeptides which form a part of the present invention, may be administered to warm blooded mammals by parenteral application either intravenously, subcutaneously or intramuscularly. These compounds are potent immunopotentiating agents with a daily dosage in the range of about 1 to 100 mg/kg of body weight per day for intravenous administration. Obviously the required dosage will vary with the particular condition being treated, the severity of the condition and the duration of treatment. A suitable dosage form for pharmaceutical use is 1 mg. of lyophilized thymosin$\alpha_1$, [[Asn$^2$]-thymosin$\alpha_1$,] or one of the aforesaid peptide fragments thereof to be reconstituted prior to use by the addition of sterile water or saline.

Also included within the scope of the present invention are the pharmaceutically acceptable salts of thymosin$\alpha_1$, [[Asn$^2$]-thymosin$\alpha_1$,] and the aforesaid peptide fragments thereof. Suitable salts include sodium, potassium or a strong organic base such as guanidine. In addition, the counter ions of these cations such as the chloride, bromide, sulfate, phosphate, maleate, acetate, citrate, benzoate, succinate, malate, ascorbate and the like, may be included in the preparation.

Abbreviations used herein have the following meaning: Boc, t-butyloxycarboxy; Bzl, benzyl; DCC, dicyclohexylcarbodiimide; DMF, dimethylformamide; THF, tetrahydrofuran; HOSu, N-hydroxysuccinimide; Triton B, 40% methanolic solution of trimethylbenzylammonium hydroxide; NMM, N-methylmorpholin; CHA, cyclohexylamine; DCHA, dicyclohexylamine; Z, benzyloxycarbonyl; Cl$_2$ 7,2,4-dichlorobenzyloxycarbonyl; DMSO, dimethylsulfoxide; and TFA, trifluoroacetic acid; TLC, thin layer chromatography.

While specific protecting groups have been employed in describing the preferred embodiment synthesis of thymosin$\alpha_1$ [and [Asn$^2$]-thymosin$\alpha_1$], it is within the skill of the art to utilize equivalent conventional protecting groups in such synthesis.

In a broader aspect of the present invention, —Ser(R$^1$) is utilized as the protected form of serine wherein R$^1$ is a conventional protecting group for the hydroxyl group of the serine residues selected from benzyl, acetyl, benzoyl, tert-butyl, trityl, 4-bromobenzyl, 2,6-dichlorobenzyl and benzyloxycarbonyl; —Asp(OR$^2$) is utilized as the protected form of aspartic acid wherein R$^2$ is a conventional protecting group for carboxyl groups selected from esters such as aryl esters, particularly phenyl or phenyl substituted with lower alkyl, halo, nitro, thio or substituted thio, i.e., methylthio, aralkyl esters such as benzyl or benzyl substituted with methoxy, halo or nitro, lower alkyl esters such as methyl, ethyl, tert-butyl and tert-amyl, substituted lower alkyl esters such as 2-haloethyl, $\beta,\beta$-dimethylaminoethyl and cyanomethyl, benzhydryl esters and phenacyl esters; —Thr(R$^3$)— is utilized as the protected form of threonine wherein R$^3$ is a conventional protecting group for the hydroxyl group of the threonine residues such as benzyl, acetyl, benzoyl, tert-butyl, trityl, 2,6-dichlorobenzyl, 4-bromobenzyl and benzyloxycarbonyl; —Glu(OR$^4$)— is utilized as the protected form of glutamic acid wherein R$^4$ is independently selected from the protecting groups set forth for R$^2$ above; —Lys(R$^5$)— is utilized as the protected form of lysine wherein R$^5$ is a conventional $\omega$-amino protecting group selected from benzyloxycarbonyl which may be optionally substituted in the aromatic ring such as by 4-chloro, 2-bromo, 4-bromo, 2,4-dichloro, 4-nitro, 4-methoxy, 3,5-dimethoxy, 4-methyl, 2,4,6-trimethyl, 4-phenylazo, 4-(4-methoxyphenylazo), 2-(N,N-dimethylcarbonamido), 4-dihydroxyboryl, and 2-nitro-4,5-dimethoxy, urethane type protecting groups such as 4-toluenesulfonylethyloxycarbonyl, 9-fluorenylmethyloxycarbonyl and related base cleavable groups, 5-benzisoxazolylmethyleneoxycarbonyl, methylthio- and methylsulfonylethyloxycarbonyl, isonicotinyloxycarbonyl, haloethyloxycarbonyl, diisopropylmethyloxycarbonyl, benzhydryloxycarbonyl, isobornyloxycarbonyl, dinitrodiphenylmethyloxycarbonyl, tert.butyloxycarbonyl, tert.—amyloxycarbonyl, adamantyloxycarbonyl, cyclopentyloxycarbonyl, methylcyclobutyloxycarbonyl, methylcyclohexyloxycarbonyl, 2-arylisopropyloxycarbonyl groups such as 2-(p-biphenylyl)-isopropyloxycarbonyl, 2-(4-pyridyl)isopropyloxycarbonyl and related nitrogen containing urethane groups; acyl groups such as formyl, trifluoroacetyl, phthaloyl, benzenesulfonyl, acetoacetyl, chloroacetyl, 2-nitrobenzoyl, 4-toluenesulfonyl, sulfenyl groups such as benzenesulfenyl, o-nitrophenylsulfenyl and related sulfenyl groups, and aryl-lower alkyl groups such as diphenylmethyl and triphenylmethyl; and —Asn-OR$^6$ is utilized as the protected form of asparagine wherein R$^6$ is a conventional carboxyl protecting group which is independently selected from the protecting groups set forth for R$^2$ above.

In a further embodiment of the present invention, thymosin$\alpha_1$ was prepared by solid phase peptide synthesis. In such embodiment commercially available benzhydrylamine resin was neutralized and acylated with N$_\alpha$-Boc-$\alpha$-benzyl-L-aspartic acid in the presence of dicyclohexylcarbodiimide to give Boc-asparaginyl resin. This amino acid resin was then benzoylated according to the procedure of Wang, J. Amer. Chem. Soc., 95, 1328 (1973) and placed into the reaction vessel of an automated peptide synthesis apparatus. The machine was then programmed to perform the solid phase synthesis to incorporate the following amino acid unit in each cycle sequentially: Boc-Glu(OBzl)-OH, Boc-Ala-OH, Boc-Glu(OBzl)-OH, Boc-Glu(OBzl)-OH, Boc-Val-OH, Boc-Val-OH, Boc-Glu(OBzl)-OH, Boc-Lys (Cl$_2$ Z)-OH, Boc-Lys(Cl$_2$Z)-OH, Boc-Glu(OBzl)-OH, Boc-Lys (Cl$_2$Z-OH, Boc-Leu-OH, Boc-Asp(OBzl)-OH, Boc-Lys (Cl$_2$Z)-OH, Boc-Thr(Bzl)-OH, Boc-Thr(Bzl)-OH, Boc-Ile-OH, Boc-Glu(OBzl)-OH, Boc-Ser(Bzl)-OH, Boc-Ser(Bzl)-OH, Ber-Thr(Bzl)-OH, Boc-Asp(OBzl)-OH, Boc-Val-OH,2x Boc-Ala-OH, Boc-Asp(OBzl)-OH, Boc-Ser(Bzl)-OH and CH$_3$COOH. Four-fold excess of each Boc-Amino acid and dicyclohexylcarbodiimide were used in each coupling reaction (120 min) and a 30 min treatment with 33% trifluoroacetic acid in CH$_2$Cl$_2$ was used as deprotecting agent for the Boc-group. The acetyl protected octacosapeptide resin of the formula Ac-Ser(Bzl)-Asp(OBzl)-Ala-Ala-Val-Asp(OBzl)-Thr(Bzl)-Ser(Bzl)-Ser(Bzl-Glu(OBzl)-Ile-Thr(Bzl)-Thr(Bzl)-Lys(Cl$_2$Z)-Asp(OBzl)-Leu-Lys(Cl$_2$Z)-Glu(OBzl)-Lys(Cl$_2$Z)-Lys(Cl$_2$Z)-Glu(OBzl)-Val-Val-Glu(OBzl)-Glu(OBzl)-Ala-Glu(OBzl)-Asp(OBzl)  CO-NH-CH(C$_6$H$_5$)

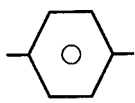

Resin thus obtained was then treated with anhydrous HF-anisole to remove all of the side chain protecting groups and at the same time to release the unprotected peptide from the resin. The crude material was desalted on a Sephadex G-10 column and then purified on a DEAE-Sephadex A-25 column eluted with a linear gradient of sodium chloride in pH7.0 Tris HCl buffer. The purified thymosin$\alpha_1$ product gave satisfactory amino acid analyses and behaved identically to the natural thymosin$\alpha_1$ on thin layer electrophoresis. It contained a very small contaminant which migrated faster than synthetic thymosin$\alpha_1$ prepared by the solution phase method. While specific protecting groups have been disclosed in regard to the solid phase synthesis, it should be noted that each amino acid can be protected by any of the protective groups discribed for the respective amino acids in solution phase synthesis.

The present invention is further illustrated by the Examples which follow.

EXAMPLE 1

Boc-Asn-OBzl

Boc-Asn-OH (11.0 g, 47.5 mmol) was dissolved in 200 ml of MeOH and 20 ml of water was added. The solution was titrated to pH 7.0 (pH paper) with a 20% aq. solution of Cs$_2$CO$_3$ (~55 ml). The mixture was evaporated to dryness and the residue reevaporated twice from DMF (120 ml each, 45°). The white solid obtained was then stirred with 8.9 g of benzyl bromide (52 mmol) in 120 ml DMF for 6 hours. On evaporation to dryness and treatment with a large volume of water, the product solidified immediately. It was collected by filtration, dissolved in ethyl acetate, washed with water, dried over Na$_2$SO$_4$, evaporated to a solid mass and crystallized from ethyl acetate with petroleum ether:

Yield, 13.8 g (90.3%); mp 120°-122°; [$\alpha$]$_D^{25}$ = -17.29° (c 1, DMF).

Anal. Calcd for C$_{16}$H$_{22}$N$_2$O$_5$ (322.36): C, 59.61; H, 6.88; N, 8.69. Found: C, 59.76; H, 6.81; N, 8.82.

EXAMPLE 2

Boc-Ala-Glu(OBzl)-OH

H-Glu(OBzl)-OH (7.0 g, 29.5 mmol) was finely ground in a mortar and pestle and then stirred with 8.88 g (32.3 mmol) of Boc-Ala-OSu for 48 hours in 250 ml DMF in the presence of 6 ml N-methylmorpholine (NMM). Some more NMM was added to maintain the reaction slightly basic during the reaction. The solvent was evaporated and the residue partitioned between 300 ml ethyl acetate and 500 ml H$_2$O containing 2 ml of 10% H$_2$SO$_4$. The organic layer was then washed three times with water, dried (Na$_2$SO$_4$) and evaporated to dryness. The product was taken up in a small volume of ether and treated with a large volume of petroleum ether. A white amorphous solid was obtained which was homogeneous on tlc:

Yield, 11.0 g (91.5%); mp 84°-88°; [$\alpha$]$_D^{25}$ = -8.08° (c 1, DMF).

Anal. Calcd for C$_{20}$H$_{28}$N$_2$O$_7$ (408.44): C, 58.81; H, 6.91; N, 6.85. Found: C, 58.89; H, 6.91; N, 6.89.

EXAMPLE 3

Boc-Ala-Glu(OBzl)-Asn-OBzl

Boc-Asn-OBzl (13.7 g, 42.4 mmol) was dissolved in 80 ml of THF and treated with 500 ml of 4 N HCl in THF. The mixture was left standing for 45 minutes during which time some product began to precipitate. On treatment with 1000 ml of ether, a white solid material formed immediately. The product was filtered and washed with ether and dried over NaOH pellets in vacuo:

Yield, 10.3 g (94%); mp 122°-126°; [$\alpha$]$_D^{25}$ = +6.82°; tlc homogeneous.

Anal. Calcd for C$_{11}$H$_{15}$N$_2$O$_3$Cl 258.71): C, 51.07; H, 5.84; N, 10.83. Found: C, 50.45; H, 5.96; N, 10.69.

Boc-Ala-Glu(OBzl)-OH (10.4 g, 25.4 mmol), HCl H-Asn-OBzl (6.56 g, 25.4 mmol) and HOSu (5.9 g, 50.8 mmol) were dissolved in DMF (250 ml, 0°). DCC (5.7 g, 27.6 mmol) was added followed immediately by Et$_3$N (3.5 ml). The mixture was stirred at 0° for 2 hours and then at 25° for 40 hours during which period some more Et$_3$N was added from time to time to maintain the reaction slightly basic. The insoluble by-products formed were filtered off and the filtrate evaporated to dryness. The residual oily material solidified on treatment with water. The crude product was taken up in CHCl$_3$, washed with water (3×), dried over Na$_2$SO$_4$ and evaporated to a smaller volume. Some solid formed at this stage was filtered off (heavily contaminated with dicyclohexylurea) and the filtrate treated with petroleum ether. A crystalline product was obtained: Yield, 8.0 g (51.4%); mp 102°-105°; $[\alpha]_D^{25} = -12.05°$ (c 1, DMF).

Anal. Calcd for C$_{31}$H$_{40}$N$_4$O$_9$ (612.66): C, 60.76; H, 6.58; N, 9.14. Found: C, 60.91; H, 6.68; N, 9.24.

EXAMPLE 4

Boc-Glu(OBzl)-Glu(OBzl)-OH

H-Glu(OBzl)-OH (4.74 g, 20 mmol) was ground in a mortar and pestle and stirred with Boc-Glu(OBzl)-OSu (8.7 g, 20 mmol) in DMF for 36 hours in the presence of 3.6 ml NMM. The ensuing solution was evaporated to a syrup and treated with water. The oily precipitate was taken up in ethyl acetate, washed successively with 5% HOAc and water (3x), dried over Na$_2$SO$_4$ and evaporated to dryness yielding 14.03 g of a clear oil. It was left standing submerged under petroleum ether. The residual oil weighed 10.2 g (90.0%). TLC indicated that the product was homogeneous. $[\alpha]_D^{25} = -7.59°$ (c 1, DMF).

Anal. Calcd for C$_{29}$H$_{36}$N$_2$O$_9$ (556.60): C, 62.57; H, 6.52; N, 5.03. Found: C, 62.37; H, 6.34; N, 5.01.

EXAMPLE 5

Boc-Glu(OBzl)-Glu(OBzl)-Ala-Glu(OBzl)-Asn-OBzl

Boc-Ala-Glu(OBzl)-Asn-OBzl (28.2 g; 46 mmol) was treated with 1.1 liter of 4 N HCl in THF for 1 hour. Evaporation of the solvent and excess acid left an oil which was evaporated twice more with fresh THF. The residual oil turned into a solid when treated with a large volume of ether. The solid HCl.H-Ala-Glu(OBzl)-Asn-OBzl was stirred with Boc-Glu(OBzl)-Glu(OBzl)-OH (25.6 g, 46 mmol), HOSu (10.6 g, 92 mmol) and DCC (10.9 g, 53 mmol) in DMF (540 ml) at 0° for 1 hour and then at 25° for 48 hours. Et$_3$N was added to maintain the reaction slightly basic over the entire period of time (~16 ml Et$_3$N total). The insoluble by-products formed were filtered off and the filtrate evaporated to dryness. The crude product was dissolved in CHCl$_3$, washed with water (3x), dried over Na$_2$SO$_4$ and evaporated to dryness. The product solidified when treated with petroleum ether. Recrystallized from i-PrOH:

Yield, 28.9 g (59.8%); mp 169°-175°; $[\alpha]_D^{25} = -11.78°$ (c 1, DMF).

Anal. Calcd for C$_{55}$H$_{66}$N$_6$O$_{15}$ (1051.13): C, 62.85; H, 6.33; N, 8.00. Found: C, 62.57; H, 6.35; N, 8.06.

EXAMPLE 6

Boc-Val-Val-OH

Boc-Val-OSu (12.6 g, 40 mmol) and H-Val-OH (4.68 g, 40 mmol) were condensed in DMF (250 ml) for 96 hours in the presence of 2 ml Et$_3$N. More Et$_3$N was added when needed to maintain the reaction slightly basic. The remaining insoluble material was filtered off and the filtrate evaporated to dryness (45°). The residue was partitioned between ether and dilute H$_2$SO$_4$ (~1%) and the organic layer washed with water (3x), dried over Na$_2$SO$_4$ and evaporated to a foamy glass. The product was crystallized from ether and petroleum ether:

Yield, 12.2 g (96.4%); mp 155°-158°; $[\alpha]_D^{25} = +1.10°$ (c 1, DMF).

Anal. Calcd for C$_{15}$H$_{28}$N$_2$O$_5$ (316.4): C, 56.94; H, 8.92; N, 8.85. Found: C, 56.64; H, 9.16; N, 8.71.

EXAMPLE 7

Boc-Glu(OBzl)-Val-Val-OH.CHA

Boc-Val-Val-OH (40.5 g, 128 mmol) was treated with 1.8 l of 4 N HCl in THF for 60 minutes. Evaporation to remove excess acid and solvent followed by treatment with ether provided 34.5 g of HCl.H-Val-Val-OH as a white amorphous powder. It was treated with Boc-Glu(OBzl)-OSu (55.6 g, 128 mmol) in 1 liter DMF for 24 hours in the presence of 54 ml Et$_3$N. The reaction mixture was filtered to remove some insoluble material and the filtrate evaporated to dryness. The remaining oily residue was taken up in EtOAc (1.5 l) and washed with 5% HOAc (2x) followed by water (3x). The organic layer was dried (Na$_2$SO$_4$) and evaporated to dryness to give a colorless clear oil which did not crystallize. It was thus dissolved in 3.2 l of ether and treated with cyclohexylamine (CHA) (17 ml) until the pH (moist pH paper) of the mixture was 7.5. The solid salt obtained was collected and recrystallized from MeOH and ether:

Yield, 58.9 g (72.7%); mp 158°-60°; $[\alpha]_D^{25} = -33.41°$ (c 1, MeOH).

Anal. Calcd for C$_{33}$H$_{54}$N$_4$O$_8$ (634.79): C, 62.44; H, 8.57; N, 8.83. Found: C, 62.18; H, 8.37; N, 8.77.

EXAMPLE 8

HCl.H-Glu(OBzl)-Glu(OBzl)-Ala-Glu(OBzl)-Asn-OBzl

Boc-Glu(OBzl)-Glu(OBzl)-Ala-Glu(OBzl)-Asn-OBzl (3.9 g, 3.48 mmol) was treated with 15 ml 4 N HCl in THF for 30 minutes. Some crystalline product started to form. Ether (210 ml) was added and the precipitated solid was collected and washed with ether. The crude material was crystallized from MeOH and ether:

Yield, 2.58 g (75.1%); mp 148°-151°; $[\alpha]_D^{25} = -3.65°$ (c 1, DMF).

Anal. Calcd for C$_{50}$H$_{58}$N$_6$O$_{13}$.HCl (987.48): C, 60.82; H, 6.02; N, 8.51. Found: C, 60.02; H, 6.18; N, 8.37.

EXAMPLE 9

Boc-Glu(OBzl)-Val-Val-Glu(OBzl)-Glu(OBzl)-Ala-Glu-(OBzl)-Asn-OBzl

Boc-Glu(OBzl)-Val-Val-OH.CHA (1.69 g, 2.66 mmol) was suspended in water (40 ml) and ethyl acetate (40 ml) in a separatory funnel when 4 ml of 1 M H$_2$SO$_4$ was added. After vigorous shaking, the solid dissolved and the organic layer was washed several times with water, dried over Na$_2$SO$_4$ and evaporated to an oil (1.45 g). The free tripeptide thus obtained was then condensed with 2.58 g of HCl.H-Glu(OBzl)-Glu(OBzl)-Ala-Glu(OBzl)-Asn-OBzl (2.61 mmol) in 15 ml DMF in the presence of HOSu (0.612 g, 5.32 mmol), NMM (0.3 ml, 2.66 mmol) and DCC (0.63, 3.06 mmol) during 1 hour at 0° and 60 hours at 25°. More NMM was added when needed to maintain the reaction slightly basic. An insoluble by-product was formed which was filtered off and the filtrate evaporated to dryness (45°). The remaining oily residue solidified when treated with water. The crude solid was dissolved in DMF (50 ml) and precipitated with MeOH (300 ml):

Yield, 2.25 g (58.7%); mp 277°–280°; $[\alpha]_D^{25} = -12.43°$ (c 1, DMF).

Anal. Calcd for $C_{77}H_{97}N_9O_{20}$ (1468.62): C, 62.97; H, 6.66; N, 8.58. Found: C, 62.72; H, 6.71; N, 8.53.

EXAMPLE 10

Boc-Lys(Z)-Lys(Z)-OH.DCHA

Boc-Lys(Z)-OH (15 g, 39.5 mmol) was stirred with HOSu (5.8 g, 50.5 mmol) and DCC (8.66 g, 42 mmol) in THF (250 ml) for 3 hours. An insoluble by-product was filtered off and the filtrate evaporated to dryness. The residual syrup (24.2 g) was treated with i-PrOH (150 ml) and petroleum ether (150 ml) to yield an oily product (21 g) which failed to crystallize. The crude active ester Boc-Lys(Z)-OSu was thus used for condensation with H-Lys(Z)-OH (10.6 g, 38 mmol) in DMF (250 ml) for 72 hours in the presence of 5.5 ml Et$_3$N. More Et$_3$N was added occasionally in order to maintain the stirred reaction mixture slightly basic. Some small quantity of undissolved material was then filtered off and the filtrate evaporated to dryness (45°). The remaining oily residue was treated with 1 liter of 5% HOAc. The product precipitated was extracted into ethyl acetate and the organic phase washed with water, dried over Na$_2$SO$_4$ and evaporated to an oil. It was crystallized from ethyl acetate (300 ml) containing DCHA (10 ml) as a salt. Recrystallized from MeOH and ether:

Yield, 22.7 g (72.5%); mp 160°–162°; $[\alpha]_D^{25} = -2.21°$ (c 1, MeOH).

Anal. Calcd for $C_{45}H_{69}N_5O_9$ (824.04): C, 65.59; H, 8.44; N, 8.50. Found: C, 65.40; H, 8.50; N, 8.39.

EXAMPLE 11

Boc-Glu(OBzl)-Lys(Z)-Lyz(Z)-OH

Boc-Lys(Z)-Lys(Z)-OH.DCHA (10 g, 12.14 mmol) was partitioned between EtOAc (1 liter) and 0.1 N H$_2$SO$_4$ (1 liter). The organic layer was then washed with water (3x), dried over Na$_2$SO$_4$ and evaporated to dryness (7.9 g). The free acid, Boc-Lys(Z)-Lys(Z)-OH, thus obtained was treated with freshly prepared 4 N HCl in THF for 30 minutes. The solvent and the excess acid was evaporated (30°) and the residue re-evaporated twice with THF. The remaining residue solidified when treated with ether. The salt HCl.H-Lys(Z)-Lys(Z)-OH was collected by filtration and washed several times with ether to yield 6.7 g of white powder. It was dissolved in DMF (70 ml), chilled in an ice-bath and treated with Et$_3$N (1.63 ml) followed by Boc-Glu(OBzl)-OSu (5.54 g, 12.76 mmol). The mixture was stirred at 0° for 1 hour and then at 25° for 24 hours. More Et$_3$N was added during this time to maintain the reaction at approximately pH 7.5 (pH paper). A few ml of acetic acid was added to make the reaction acidic (pH 3.5) and the solvent removed by evaporation. The ensuing residue was taken up in EtOAc, washed with water (3x), dried over Na$_2$SO$_4$ and evaporated to dryness when the product began to solidify. It was triturated in ether and recrystallized from ethyl acetate:

Yield, 7.26 g (69.5%); mp 153°–155°; $[\alpha]_D^{25} = -2.71°$ (c 1, THF).

Anal. Calcd for $C_{45}H_{59}N_5O_{12}$ (861.96): C, 62.70; H, 6.90; N, 8.12. Found: C, 62.51; H, 6.93; N, 8.13.

EXAMPLE 12

Boc-Glu(OBzl)-Lys(Z)-Lys(Z)-Glu(OBzl)-Val-Val-Glu(OBzl)-Glu(OBzl)-Ala-Glu(OBzl)-Asn-OBzl

Boc-Glu(OBzl)-Val-Val-Glu(OBzl)-Glu(OBzl)-Ala-Glu(OBzl)-Asn-OBzl. (1.7 g, 1.16 mmol) was treated with TFA (24 ml) for 30 minutes. After evaporation of the excess acid (30°) the residue was triturated with ether. The powder obtained was washed thoroughly with ether and petroleum ether and dried over NaOH in vacuo to give the trifluoroacetate salt of the octapeptide (1.71 g). The active ester Boc-Glu(OBzl)-Lys(Z)-Lys(Z)-OSu was then generated in situ by stirring Boc-Glu(OBzl)-Lys(Z)-Lys(Z)-OH (0.998 g, 1.16 mmol), HOSu (0.16 g, 1.4 mmol) and DCC (0.274 g, 1.33 mmol) in 15 ml DMF at 0° for 3 hours. To this solution containing the tripeptide active ester, the octapeptide salt CF$_3$COOH.H-Glu(OBzl)-Val-Val-Glu(OBzl)-Glu(OBzl)-Ala-Glu(OBzl)-Asn-OBzl (1.71 g) was added together with 0.2 ml of Et$_3$N. A few more drops of Et$_3$N and DMF (15 ml) were added and the reaction was stirred for 3 days at 25°. A gelatinous semi-solid formed. It was acidified with acetic acid and treated with water. The white solid precipitate was collected and washed (H$_2$O, MeOH, Ether) to yield 2.25 g of crude product melting at 310°–313°. It was dissolved in DMF and precipitated with MeOH:

Yield, 1.75 g (68.3%); mp 314°–316°; $[\alpha]_D^{25} = -13.78°$ (c 1, DMSO); homogeneous on tlc.

Anal. Calcd for $C_{117}H_{146}N_{14}O_{29}$ (2212.45): C, 63.51; H, 6.65; N, 8.86. Found: C, 63.31; H, 6.78; N, 8.87.

Amino Acid Anal. Asp, 1.06; Glu, 5.00; Ala, 1.06; Val, 2.15; Lys, 1.87; NH$_3$, 1.06.

EXAMPLE 13

Boc-Leu-Lys(Z)-OH.DCHA

Boc-Leu-OSu (4.0 g, 12.2 mmol) and H-Lys(Z)-OH (3.42 g, 12.2 mmol) were condensed in DMF (75 ml) during 48 hours in the presence of Et$_3$N (1.7 ml). The reaction pH was maintained at 7.5 (moist pH paper) by addition of Et$_3$N periodically as usual. The remaining insoluble material was filtered off and the filtrate evaporated to dryness. The ensuing foamy glass was dissolved in ether (200 ml) and the mixture treated with 3 ml of DCHA to produce crystalline material which was collected, washed with ether and recrystallized from MeOH and ether:

Yield, 5.7 g (69.5%); mp 140°–142°; $[\alpha]_D^{25} = -7.20°$ (c 1, MeOH).

Anal. Calcd for $C_{37}H_{62}N_4O_7$ (674.90): C, 65.85; H, 9.26; N, 8.30. Found: C, 65.80; H, 9.07; N, 8.15.

EXAMPLE 14

Boc-Asp(OBzl)-Leu-Lys(Z)-OH

Boc-Leu-Lys(Z)-OH.DCHA (2.97 g, 4.4 mmol) was converted into the free acid (partitioned between EtOAc and 0.1 N H$_2$SO$_4$) and the colorless oil obtained (2.2 g) was treated with 4 N HCl in THF (40 ml) for 30 minutes. The excess acid and the solvent were evaporated (30°) and the residue treated with ether. The remaining oil was dissolved in ether and evaporated twice more with fresh ether. The residue was then stirred with Boc-Asp(OBzl)-OSu (1.85 g, 4.4 mmol) in the presence of Et$_3$N (1.85 ml) overnight. The reaction mixture was then evaporated to dryness giving an oily residue which was taken up in ethyl acetate, washed with water (3x), dried over $Na_2SO_4$ and evaporated to dryness again. The crude product thus obtained was crystallized from ethyl acetate and petroleum ether:

Yield, 1.52 g (49.6%); mp 109°-111°; $[\alpha]_D^{25} = -16.14°$ (c 1, DMF).

Anal. Calcd for $C_{36}H_{50}N_4O_{10}$ (698.91): C, 61.88; H, 7.21; N, 8.02. Found: C, 61.72; H, 7.17; N, 8.01.

EXAMPLE 15

Boc-Asp(OBzl)-Leu-Lys(Z)-Glu(OBzl)-Lys(Z)-Lys(Z)-Glu(OBzl)-Val-Val-Glu(OBzl)-Gl(OBzl)-Ala-Glu(OBzl)-Asn-OBzl

Boc-Glu(OBzl)-Lys(Z)-Lys(Z)-Glu(OBzl)-Val-Val-Glu(OBzl)-Glu(OBzl)-Ala-Glu(OBzl)-Asn-OBzl (1.2 g, 0.545 mmol) was treated with 35 ml TFA for 30 minutes. The excess acid was quickly evaporated and the residue triturated with ether several times to give 1.2 g of undecapeptide TFA-salt as a white powder. It was dissolved in a mixture of DMF (5 ml) and DMSO (2 ml) and treated with Boc-Asp(OBzl)-Leu-Lys(Z)-Osu generated in situ by stirring Boc-Asp(OBzl)-Leu-Lys(Z)-OH (0.381 g, 0.545 mmol) with HOSu (0.126 g, 1.1 mmol) and DCC (0.124 g, 0.599 mmol) in 3 ml DMF at 0° for 3 hours. The mixture containing the tripeptide active ester and undecapeptide was stirred at 0° for 2 hours and then at 25° for 3 days, during which period $Et_3N$ was added from time to time in order to maintain the pH slightly basic. A gelatenous substance formed. It was triturated with 5% HOAc and the resulting white solid was filtered and washed with water, MeOH and ether to give 1.28 g of crude material melting at 325°-326°. Reprecipitation from DMF-DMSO (10 ml and 5 ml) and MeOH (230 ml) yielded 1.22 g (80.2%); mp 326°-327°; $[\alpha]_D^{25} = -15.71°$ (C 1, DMF-DMSO).

Anal. Calcd for $C_{148}H_{186}N_{18}O_{36}$ (2793.21): C, 63.64; H, 6.71; N, 9.03. Found: C, 62.78; H, 6.75; N, 9.04.

Amino Acid Anal. Asp, 2.00; Glu, 5.65; Ala, 1.12; Val, 2.24; Leu, 0.84; Lys, 3.00; $NH_3$, 1.02.

EXAMPLE 16

Glu-Val-Val-Glu-Glu-Ala-Glu-Asn

Boc-Glu(OBzl)-Val-Val-Glu(OBzl)-Glu(OBzl)-Ala-Glu(OBzl)-Asn-OBzl (0.72 g, 0.49 mmol) was hydrogenated over 5% $Pd/BaSO_4$ (0.5 g) for 3 hours at 50 psi in $DMF-MeOH-H_2O$ (40 ml-30 ml-2 ml). The mixture was then filtered and the filtrate evaporated to dryness. It was subsequently treated with 5 ml of TFA for 30 minutes and the residue obtained after evaporation of the acid was triturated several times with ether. The ensuing white solid was taken up in water (20 ml) and lyophilized to give 0.47 g of crude product. The compound was loaded on a Bio-Rad AG1-X 2 column (3×32 cm) equilibrated with pH 8.1 ammonium acetate buffer (2% HOAc made to pH 8.1 with $NH_3$). The column was eluted successively with 200 ml each of 0.025 M pH 5.5 $NH_4OAc$, 0.025 M HOAc, 0.05 M HOAc, 0.1 M HOAc, 0.25 M HOAc, 0.5 M HOAc, 0.75 M HOAc, 1 M HOAc. Fractions of 12 ml were collected and the eluate from each tube was monitored by thin layer chromatogram. The fractions containing the desired material (tube 225-229) were pooled and lypholized twice to yield 0.223 g (48.1%) of the pure product. Homogeneous on tlc and paper electrophoresis.

Anal. Calcd for $C_{37}H_{59}N_9O_{18}.3H_3O$ (971.96): C, 45.71; H, 6.74; N, 12.97. Found: C, 45.57; H, 6.83; N, 12.51.

Amino Acid Anal. Asp, 1.00; Glu, 3.95; Ala, 1.00; Val, 1.91; $NH_3$, 1.00.

EXAMPLE 17

Glu-Lys-Lys-Glu-Val-Val-Glu-Glu-Ala-Glu-Asn

Boc-Glu(OBzl)-Lys(Z)-Lys(Z)-Glu(OBzl)-Val-Val-Glu(OBzl)-Glu(OBzl)-Ala-Glu (OBzl)-Asn-OBzl (0.5 g, 0.226 mmol) was dissolved in 2 ml of TFA and stirred with 15 ml of HF at 0° for 15 minutes. After evaporation of excess acid (0°), the residue was dissolved in 5% aqueous HOAc, washed with ether (3x), evaporated to a smaller volume and lyophilized to yield 0.34 g of crude product. It was chromatographed on the ion-exchange column as described above (see Example 16) to give 0.13 g (42.1%) of pure material: $[\alpha]_D^{25} = -85.65°$ (c 1, $H_2O$).

Anal. Calcd for $C_{54}H_{90}N_{14}O_{23}.4H_2O$ (1375.43): C, 47.15; H, 7.18; N, 14.25. Found: C, 47.03; H, 7.03; N, 13.88.

Amino Acid Anal. Asp, 1.03; Glu, 5.03; Ala, 0.94; Val, 2.06; Lys, 2.05; $NH_3$, 1.06.

EXAMPLE 18

Asp-Leu-Lys-Glu-Lys-Lys-Glu-Val-Val-Glu-Glu-Ala-Glu-Asn

Boc-Asp(OBzl)-Leu-Lys(Z)-Glu(OBzl)-Lys(Z)-Lys(Z)-Glu(OBzl)-Val-Val-Gl(OBzl)-Glu(OBzl)-Ala-Glu(OBzl)-Asn-OBzl (1.128 g, 0.404 mmol) was mixed with 7 ml of anisole and treated with 25 ml anhydrous HF at 0° for 15 minutes. The excess acid was evaporated (0°) and the remaining residue partitioned between ether and water. The water layer was washed twice with ether, evaporated to ½ the original volume and lypholized to provide 0.69 g of crude material. It was chromatographed in the manner described above for compounds in Examples 16 and 17. The material eluted at tubes 101-120 was collected and lyophilized to give 0.25 g of product which was shown to be slightly contaminated with minor impurities. It was thus rechromatographed on the same column to give 0.155 g (22%) of pure product. Paper electrophoresis indicated it was homogeneous. $[\alpha]_D^{25} = -86.27°$ (c 1, 0.1 N HCl).

Anal. Calcd for $C_{70}H_{118}N_{18}O_{28}.5H_2O$ (1749.86): C, 48.04; H, 7.37; N, 14.41. Found: C, 47.90; H, 7.53; N, 14.49.

Amino Acid Anal. Asp, 1.98; Glu, 5.09; Ala, 1.04; Val, 2.02; Leu, 0.97; Lys, 2.89; $NH_3$, 1.09.

EXAMPLE 19

Ac-Ser(Bzl)-OH.DCHA

H-Ser(Bzl)-OH (18.6 g, 95.4 mmol) was dissolved in 45 ml of Triton B (40% methanolic solution of Trimethylbenzylammonium Hydroxide), evaporated to dryness and the residue re-evaporated twice with DMF (250 ml each). The oily residue was taken up in DMF (250 ml) and stirred with Ac-OSu (16.5 g, 95.4 mmol) for 5 hr. A few ml (~5 ml) of NMM was added to bring the reaction to slightly basic conditions during this period of time. Acetic acid (~5 ml) was then added and the solvents removed by evaporation, leaving an oily residue which was partitioned between 5% HOAc and EtOAc. The aqueous layer was extracted once more with EtOAc and the combined EtOAc solution washed twice with small volumes of H$_2$O, dried over Na$_2$SO$_4$, and evaporated to approximately 300 ml ($\frac{1}{3}$ of original volume). Crystalline product formed immediately when DCHA was added to a slightly basic condition (~35 ml). The crude material (32.5 g, mp 135°–145°) was recrystallized from EtOH (150 ml) and ether (900 ml): Yield, 17.8 g (44.7%); mp 166°–168°; $[\alpha]_D^{25} = +34.18°$ (c 1, MeOH).

Anal. Calcd for C$_{24}$H$_{38}$N$_2$O$_4$ (418.56): C, 68.87; H, 9.15; N, 6.69. Found: C, 68.54; H, 9.38; N, 6.85.

EXAMPLE 20

HCl.H-Ser(Bzl)-OBzl

Boc-Ser(Bzl)-OH (6.3 g, 21.4 mmol) was dissolved in MeOH (75 ml) and H$_2$O (7.5 ml). To this solution, 20% Cs$_2$CO$_3$ was added until neutral (pH 7.0; 28 ml) and then the solvents were removed by evaporation. The residue obtained was re-evaporated twice with DMF (50 ml each) and the salt was stirred with benzyl bromide (4.28 g, 25 mmol) in 25 ml DMF for 15 hr. Evaporation of the solvent gave an oily residue which was extracted into EtOAc, washed with H$_2$O (3 times), dried over Na$_2$SO$_4$, and evaporated to dryness leaving a colorless clear oil (8.9 g). The compound did not crystallize at this stage. It was thus converted into the HCl salt by deprotection of the Boc-group as usual (30 min. treatment with 4 N HCl in THF). On work-up, a white solid mass was obtained which on recrystallization gave 4.99 g (72.8%) of the title compound: mp 138°–140°; $[\alpha]_D^{25} = -23.86°$ (c 1, MeOH).

Anal. Calcd for C$_{17}$H$_{20}$NO$_3$Cl (321.80); C, 63.45; H, 6.26; N, 4.35. Found: C, 63.30; H, 6.02; N, 4.15.

EXAMPLE 21

Ac-Ser(Bzl)-OBzl

HCl.H-Ser(Bzl)-OBzl (3.38 g, 10.5 mmol) was dissolved in 50 ml of DMF and treated with Ac-OSu (1.73 g, 11 mmol) followed by 3 ml of Et$_3$N. The mixture was stirred for 18 hours and then acidified with a few ml of HOAc. Evaporation of the solvent left an oil which was partitioned between EtOAc and 5% HOAc. The organic layer was washed with H$_2$O (3 times), dried over Na$_2$SO$_4$, and evaporated to a clear oil which on treatment with petroleum ether solidified immediately (3.2 g). The product was recrystallized from EtOAc and petroleum ether to to yield, 2.7 g (78.6%); mp 89°–91°; $[\alpha]_D^{25} = -14.91°$ (c 1, MeOH).

Anal. Calcd for C$_{19}$H$_{21}$NO$_4$ (327.38): C, 69.71; H, 6.47; N, 4.28. Found: C, 69.55; H, 6.37; N, 4.37.

The same compound was also prepared by a different route. Thus, H-Ser(Bzl)-OH (18.6 g, 95.4 mmol) was dissolved in 45 ml Triton B, evaporated to dryness, and the residue re-evaporated twice with DMF (100 ml each). The residue was then stirred with Ac-OSu (16.9 g, 95.4 mmol) in 150 ml DMF for 20 hours. N-Methylmorpholin was added from time to time in order to maintain the reaction slightly basic. Removal of the solvent and extraction of the product into EtOAc followed by washing with small volumes of 10% HOAc, H$_2$O (the product is water soluble, use a small volume of H$_2$O), dried over Na$_2$SO$_4$, evaporation to dryness again gave a clear oil (14.5 g, Ac-Ser(Bzl)-OH). The compound failed to crystallize. It was thus dissolved in a mixture of MeOH and H$_2$O (300 ml:30 ml), titrated to pH 7.0 with 20% Cs$_2$CO$_3$ and evaporated to a solid mass. The salt was re-evaporated twice more with DMF and stirred with benzyl bromide (15.4 g, 91 mmol) in 250 ml DMF for 18 hours. On evaporation of the solvent, the residue was taken up in H$_2$O (600 ml) and the oily product formed was extracted into EtOAc. It was washed with H$_2$O, dried over Na$_2$SO$_4$ and evaporated to a syrup which on seeding crystallized immediately. It was recrystallized from EtOAc and petroleum ether to yield, 10.42 g (32.2% overall); mp 89°–91°.

EXAMPLE 22

Ac-Ser(Bzl)-HNNH$_2$

Ac-Ser(Bzl)-OBzl(2.2 g, 6.73 mmol) was dissolved in 75 ml EtOH and stirred gently with 5 ml of H$_2$NNH$_2$ overnight. Some insoluble matter precipitated was filtered off and the filtrate evaporated to an oil which solidified when treated with ether. The product was recrystallized from a small volume of EtOH and ether to yield, 1.40 g (82.8%); mp 128°–130°; $[\alpha]_D^{25} = +5.80°$ (c 1, MeOH).

Anal. Calcd for C$_{12}$H$_{17}$N$_3$O$_3$ (251.28): C, 57.36; H, 6.82; N, 16.72. Found: C, 57.13; H, 6.87; N, 16.74.

EXAMPLE 23

Boc-Ala-Ala-OH

L-Alanine (3.57 g, 40 mmol) was dissolved in 18.8 ml of Triton B (40 mmol), evaporated to dryness, and the oily residue re-evaporated twice with DMF (30 ml each). The salt obtained was stirred with 11.45 g of Boc-Ala-OSu (40 mmol) in 40 ml DMF, with 4 ml of NMM added, for 20 hours. The solvent was removed and the residue taken up in 10% HOAc (100 ml). The product was extracted into EtOAc (4 times 100 ml), washed twice with a small volume of H$_2$O, dried over Na$_2$SO$_4$, evaporated to a small volume, and treated with petroleum ether until cloudiness developed. A crystalline product formed on storage in the refrigerator overnight: Yield, 8.2 g (76.3%); mp 115°–118°.

Anal. Calcd for C$_{11}$H$_{20}$N$_2$O$_5$.$\frac{1}{2}$H$_2$O (269.30): C, 49.05; H, 7.86; N, 10.39. Found: C, 48.90; H, 7.93; N, 10.15.

EXAMPLE 24

HCl.H-Ala-Ala-OH

Boc-Ala-Ala-OH (36.2 g, 139 mmol) was treated with 3 liters of 4 N HCl in THF for 30 minutes. Evaporation and work-up as usual gave an oily mass which solidified when treated with ether. The product was recrystallized from methanol with ether to yield 9.1 g (33.3%); mp 209°–211°.

Anal. Calcd for C$_6$H$_{13}$N$_2$O$_3$Cl (196.64): C, 36.65; H, 6.66; N, 14.25. Found: C, 36.85; H, 6.80; N, 14.02.

EXAMPLE 25

Boc-Ala-Ala-OBzl

Boc-Ala-Ala-OH (7.23 g, 27.8 mmol) was dissolved in a mixture of 200 ml MeOH and 20 ml H$_2$O.Cs$_2$CO$_3$ solution (20% aqueous) was added until the pH reached 7.0 (~30 ml) and the resultant neutral solution evaporated to dryness. The residue was re-evaporated twice with DMF (150 ml) and the gelatenous solid that remained was stirred in 120 ml DMF with benzyl bromide (7.2 g, 42 mmol) for 15 hours. The solvent was then removed by evaporation and the residue treated with 500 ml water. The product precipitated as an oil which gradually solidified on standing. It was taken up in EtOAc (400 ml), washed with H$_2$O (3 times), dried (Na$_2$SO$_4$), and evaporated to a syrup which on treatment with petroleum ether began to crystallize. The product was recrystallized from EtOAc and petroleum ether to yield, 7.2 g (73.8%); mp 71°-73° (lit. mp 73°-74°; D. A. Laufer et al., *J. Amer. Chem. Soc.*, 90, 2696 (1968)).

EXAMPLE 26

HCl.H-Ala-Ala-OBzl

Boc-Ala-Ala-OBzl (6.0 g, 17.15 mmol) was treated with 380 ml of freshly prepared 4 N HCl in THF for 30 minutes. The excess acid and solvent were evaporated off and the remaining syrup re-evaporated twice with fresh THF. The residue solidified immediately when treated with ether. It was recrystallized from MeOH and ether to yield, 4.30 g (87.4%); mp 154°-156°; $[\alpha]_D^{25} = -38.86°$ (c 1, MeOH).

Anal. Calcd for $C_{13}H_{19}N_2O_3Cl$ (286.76): C, 54.45; H, 6.68; N, 9.77. Found: C, 54.44; H, 6.73; N, 9.98.

EXAMPLE 27

Boc-Asp(OBzl)-Ala-Ala-OH.DCHA

HCl.H-Ala-Ala-OH (2.36 g, 12 mmol) was dissolved in 20 ml of DMF, chilled in an ice-bath, and treated with 1.68 ml of Et$_3$N (12 mmol) followed by Boc-Asp(OBzl)-OSu (12 mmol). The mixture was stirred gently at 0° for 2 hours and then at 25° overnight during which time one more equivalent of Et$_3$N (12 mmol) was added, in small proportions, maintaining the reaction pH near 8.0. A few ml of HOAc was added and the acidified mixture evaporated to dryness. The product formed was extracted into EtOAc, washed with H$_2$O (3 times), dried over Na$_2$SO$_4$, and evaporated to an oily residue (6 g). It was dissolved in EtOAC and titrated to pH 8.0 with DCHA. The crystalline salt precipitated and was recrystallized from i-PrOH and petroleum ether to yield, 5.1 g (65.7%); mp 138°-141°; $[\alpha]_D^{25} = -13.33°$ (c 1, MeOH).

Anal. Calcd for $C_{34}H_{54}N_4O_8$ (646.80): C, 63.14; H, 8.42; N, 8.66. Found: C, 63.00; H, 8.28; N, 8.76.

EXAMPLE 28

Ac-Ser(Bzl)-Asp(OBzl)-Ala-Ala-OH

Boc-Asp(OBzl)-Ala-Ala-OH.DCHA (3.5 g, 5.4 mmol) was partitioned between 500 ml EtOAc and 350 ml H$_2$O containing 10 ml of 10% H$_2$SO$_4$. The aqueous layer was extracted once more with EtOAc (250 ml) and the combined EtOAc layer washed twice with H$_2$O, dried over Na$_2$SO$_4$, and evaporated to dryness, leaving a glassy solid of Boc-Asp(OBzl)-Ala-Ala-OH (2.5 g). This material was treated with 200 ml of freshly prepared 4 N HCl in THF for 30 minutes, evaporated at 32° to a syrup, and re-evaporated twice more with THF. The oily residue solidified when treated with ether. This hydrochloride salt of H-Asp(OBzl)-Ala-Ala-OH (1.93 g, 4.83 mmol) was then used in the next reaction involving azide coupling with Ac-Ser(Bzl)-N$_3$ that was prepared from 1.24 g Ac-Ser(Bzl)-HNNH$_2$ (4.9 mmol) in 25 ml DMF (−25°) with 7.42 ml of 3.3 N HCl in THF (24.5 mmol) and 0.99 ml of i-amylnitrite (7.35 mmol) stirred at −30° for 30 minutes. The azide solution prepared was cooled down to −35°, mixed with 4.1 ml of Et$_3$N and then treated with the white powder of HCL.H-Asp(OBzl)-Ala-Ala-OH (1.93 g) prepared above. The mixture was stirred at −20° for 30 minutes and then at 4° for 2 days. Some more Et$_3$N was added to keep the reaction slightly basic. Work-up as usual gave a crystalline mass which was recrystallized from THF and petroleum ether to yield, 1.85 g (65.6%); mp 167°-170°; $[\alpha]_D^{25} = -18.91°$ (c 1, DMSO).

Anal. Calcd for $C_{29}H_{36}N_4O_9$ (584.61): C, 59.58; H, 6.21; N, 9.58. Found: C, 59.35; H, 6.09; N, 9.59.

EXAMPLE 29

Ac-Ser(Bzl)-Asp(OBzl)-Ala-Ala-HNNH$_2$

Ac-Ser(Bzl)-Asp(OBzl)-Ala-Ala-OH (0.825 g, 1.41 mmol) was dissolved in 4 ml DMF and chilled to 0° in an ice-bath. To the solution, H$_2$NNH$_2$ (54.3 mg; 1.69 mmol) was added followed by HOBT.H$_2$O (0.475 g, 3.10 mmol) and DCC (0.32 g, 1.55 mmol). The mixture was adjusted to pH 7.5 (wet pH paper) with NMM and stirred at 0° for 2 hours followed by 17 hours at 25°. The reaction became a gel during this time. It was diluted with MeOH and the solid material remaining was collected on a suction filter and washed thoroughly with MeOH, ether and petroleum ether to give a material melting at 229°-232°. The product was then precipitated from DMF and MeOH to yield, 0.51 g (61.0%); mp 230°-232°; $[\alpha]_D^{25} = -17.94°$ (c 1, DMSO).

Anal. Calcd for $C_{29}H_{38}N_6O_8$ (598.66): C, 58.18; H, 6.40; N, 14.04. Found: C, 58.01; H, 6.38; N, 14.17.

EXAMPLE 30

Boc-Ser(Bzl)-Asp(OBzl)-Ala-Ala-HNNH$_2$

Boc-Ser(Bzl)-Asp(OBzl)-Ala-Ala-OH (0.55 g, 0.86 mmol) in DMF (4 ml) at 0° was treated with H$_2$NNH$_2$ (32.9 mg, 1.03 mmol), HOBT.H$_2$O (288.2 mg, 1.88 mmol), and DCC (193.9 mg, 0.941 mmol). The mixture was brought to pH 7.5 with a few drops of NMM and then stirred at 0° for 2 hours followed by 25° for 17 hours. The solid by-products formed were filtered off and the filtrate evaporated to dryness. The oily residue was crystallized from i-PrOH twice: Yield, 0.13 g (23.1%); mp 184°-187°; $[\alpha]_D^{25} = -14.22°$ (c 1, DMSO).

Anal. Calcd for $C_{32}H_{44}N_6O_9$ (656.74); C, 58.52; H, 6.75; N, 12.80. Found: C, 58.55; H, 6.68; N, 12.68.

EXAMPLE 31

Boc-Asn-Ala-Ala-OBzl

HCl.H-Ala-Ala-OBzl (4.25 g, 14.83 mmol) was dissolved in DMF (60 ml), cooled to 0°, and stirred with Boc-Asn-OH (3.45 g, 14.83 mmol), HOBT (4.02 g, 29.6 mmol), NMM (2 ml) and DCC (3.37 g, 16.35 mmol) at 0° for 2 hours and then at 25° for 20 hours. More NMM was added from time to time in order to maintain the reaction slightly basic. The insoluble by-products formed was filtered off and the filtrate evaporated to dryness. The oily residue solidified immediately when treated with water. It was taken up in EtOAc, washed with H$_2$O (3 times), dried (Na$_2$SO$_4$), and evaporated to a smaller volume when the product began to crystallize. Equal volumes of petroleum ether was added and the mixture was left to stand overnight. The crude product was recrystallized from THF and petroleum ether: yield, 5.2 g (75.6%); mp 153°-155°; $[\alpha]_D^{25} = -55.61$ (c 1, MeOH).

Anal. Calcd for $C_{22}H_{32}N_4O_7$ (464.51): C, 56.89; H, 6.94; N, 12.06. Found: c, 56.66; H, 7.08; N, 11.81.

EXAMPLE 32

Ac-Ser(Bzl)-Asn-Ala-Ala-OBzl

Boc-Asn-Ala-Ala-OBzl (2.2 g, 4.75 mmol) was treated with 220 ml of 4.0 N HCl in THF for 30 minutes.

The excess acid and solvent were evaporated off and the residue re-evaporated twice with fresh THF. The oily product solidified when treated with ether. It was triturated with more fresh ether and collected to give a white powder (1.85 g). The hydrochloride salt thus obtained was dissolved in 40 ml DMF and chilled to 0° when Ac-Ser(Bzl)-OH.DCHA (1.97 g, 4.75 mmol) was added. After stirring at 0° for 30 minutes, precipitation of DCHA.HCl was observed and HOBT (1.19 g) was added followed by DCC (1.08 g, 5.23 mmol). The reaction was then adjusted to pH 7.5 (wet pH paper) with a few drops of NMM and stirred at 0° for 2 hours and then at 25° overnight. The insoluble by-product was removed by filtration and the filtrate evaporated to a slightly colored solid mass. It was washed thoroughly with H$_2$O and EtOAc to give a buff colored powder which was crystallized from DMF (40 ml) and i-PrOH (500 ml): yield, 1.57 g (56.9%); mp 213°-215°; $[\alpha]_D^{25} = -23.11°$ (c 1, DMSO).

Anal. Calcd for C$_{29}$H$_{37}$N$_5$O$_8$ (583.63): C, 59.68; H, 6.39; N, 12.00. Found: C, 59.36; H, 6.59; N, 11.97.

EXAMPLE 33

Ac-Ser(Bzl)-Asn-Ala-Ala-HNNH$_2$

Ac-Ser(Bzl)-Asn-Ala-Ala-OBzl (1.57 g, 2.69 mmol) was dissolved in 20 ml DMF and stirred with 2 ml of H$_2$NNH$_2$ for 18 hours. The solid product formed was collected and washed thoroughly with DMF, EtOH, and ether: yield, 1.22 g (89.6%); mp 262°-264°; $[\alpha]_D^{25} = -26.70°$ (c 1, DMSO).

Anal. Calcd for C$_{22}$H$_{33}$N$_7$O$_7$ (507.54): C, 52.06; H, 6.55; N, 19.32. Found: C, 51.48; H, 6.58; N, 19.22.

EXAMPLE 34

Ac-Ser(Bzl)-Asp(OBzl)-Ala-Ala-OBzl

HCl.H-Ala-Ala-OBzl (1.68 g, 5.83 mmol) was dissolved in a mixture of DMF (8 ml) and CH$_2$Cl$_2$ (20 ml) then cooled in an ice-bath. NMM (0.6 ml), Boc-Asp(OBzl)-OH (1.88 g, 5.83 mmol), and DCC (1.27 g, 6.14 mmol) were added in that order and the mixture stirred at 0° for 2 hours and then at 25° for 15 hours during which time a few more drops of NMM was added in order to maintain the reaction slightly basic. The insoluble by-products were filtered off and the filtrate evaporated to dryness. The residue was extracted into EtOAc, washed with H$_2$O (3 times), dried over Na$_2$SO$_4$, and evaporated to an oil. It was taken up in THF (55 ml), filtered to remove residual dicyclohexylurea, and evaporated to a clear oil (3.3 g). The product Boc-Asp(OBzl)-Ala-Ala-OBzl did not crystallize. It was then treated with 200 ml freshly prepared 4.0 HCl in THF for 30 minutes and worked-up as usual to give HCl.H-Asp(OBzl)-Ala-Ala-OBzl (1.89 g, 3.85 mmol) as an amorphous powder. The tripeptide ester hydrochloride was then dissolved in DMF (22 ml), chilled in an ice-bath, and stirred with Ac-Ser(Bzl)-OH.DCHA (1.61 g, 3.85 mmol) for 30 minutes followed by addition of HOBT (1.04 g, 7.7 mmol), NMM (0.4 ml), and DCC (0.82 g, 4.24 mmol). The mixture was stirred at 0° for 2 hours and then at 25° for 17 hours. The insoluble by-products formed were filtered off and the filtrate evaporated to dryness. The solid mass remaining was dissolved in EtOAc, washed with H$_2$O, 5% NaHCO$_3$, 5% HOAc, H$_2$O, and dried over Na$_2$SO$_4$. On evaporation to a smaller volume, a crystalline product started to form. The solution was treated with equal volumes of 25% petroleum ether in EtOAc and left standing to complete the crystallization. The product was recrystallized from i-PrOH and pentane to yield, 0.91 g (23.2%); mp 154°-158°; $[\alpha]_D^{25} = -35.95°$ (c 1, MeOH).

Anal. Calcd for C$_{36}$H$_{42}$N$_4$O$_9$ (674.73): C, 64.08; H, 6.27; N, 8.30. Found: C, 63.86; H, 6.24; N, 8.22.

EXAMPLE 35

Ac-Ser-Asp-Ala-Ala-OH

Ac-Ser(Bzl)-Asp(OBzl)-Ala-Ala-OBzl (0.6 g, 0.888 mmol) was hydrogenated in a Parr apparatus at 50 psi in the presence of 0.62 g catalyst (5% Pd on BaSO$_4$) in a solvent mixture consisting of 35 ml MeOH, 15 ml H$_2$O, and 1 ml HOAc for 4 hours. The catalyst was filtered off and the filtrate concentrated to a smaller volume and lyophilized to give 0.38 g crude material. Tlc showed two minor contaminants in addition to the major component. The compound was then purified on a Bio-Rad AG1×2 column (3×24 cm) which was washed with 0.2 M NaOH, H$_2$O, 0.2 M HOAc, and equilibrated with pH 8.5 buffer of 0.025 M ammonium acetate. The sample was applied at this pH and the column eluted with 250 ml each of the following acetic acid solutions in the order of: 0.25 M, 0.5 M, 1.0 M, 1.5 M, 2.0 M, 2.5 M, 3.0 M, 3.5 M, 4.0 M, and 4.5 M. The flow rate was adjusted to approximately 50 ml/hr and each 10 ml fraction was collected into an LKB fraction collector. The compound was located by spotting a 5 μl portion from each tube on silica get tlc plate (Merck 60, F-254) and developed in the solvent system of n-BuOH:HOAc:EtOAc:-H$_2$O (1:1:1:1) and then stained with chlorine-tolidine reaction. The fractions containing the major component were pooled and lyophilized twice to give 310 mg (86.3%) of the desired product; $[\alpha]_D^{25} = -77.01°$ (c 1, 10% HOAc).

Anal. Calcd for C$_{15}$H$_{24}$N$_4$O$_9$ (404.37): C, 44.55; H, 5.98; N, 13.86. Found: C, 44.25; H, 5.98; N, 13.76.

EXAMPLE 36

Ac-Ser-Asn-Ala-Ala-OH

Ac-Ser(Bzl)-Asn-Ala-Ala-OBzl (0.58 g, 0.992 mmol) was dissolved in a solvent mixture of MeOH (35 ml), DMF (5 ml), H$_2$O (15 ml) and HOAc (1.5 ml) and then hydrogenated as described above at 50 psi for 5 hours in the presence of 1.5 g catalyst. The catalyst was filtered off and the filtrate evaporated to a smaller volume and lyophilized to give 0.411 g of crude product. It was purified on the same column with the same process as described for Ac-Ser-Asp-Ala-Ala-OH (BioRad AG1×2 ion-exchange). The main fraction was pooled and lyophilized: yield, 288 mg (72.2%); $[\alpha]_D^{25} = -83.61°$ (c 1, 10% HOAc).

Anal. Calcd for C$_{15}$H$_{25}$N$_5$O$_8$ (403.39): C, 44.66; H, 6.25; N, 17.36. Found: C, 44.42; H, 6.35; N, 17.16.

EXAMPLE 37

Boc-Ser(Bzl)-Glu(OBzl)-OH.CHA

H-Glu(OBzl)-OH (39.4 g, 166 mmol) was stirred with Boc-Ser(Bzl)-OSu (65.0 g, 166 mmol) in 900 ml DMF overnight in the presence of Et$_3$N (2.3 ml, 165 mmol). More Et$_3$N was added during this time in order to maintain the reaction slightly basic. The clear solution was evaporated to dryness and the oily residue partitioned between EtOAc (1.5 liters) and 5% HOAc (2 liters). The organic layer was washed with H$_2$O (2 times), dried over Na$_2$SO$_4$, and concentrated to a clear oil (90.0 g) which was taken up in 3 liters of ether and treated with 25 ml of cyclohexylamine The solid formed was recrystallized from MeOH and ether: yield, 76.2 (74.8%); mp 154°–156.5°; $[\alpha]_D^{25}=+6.32°$ (c 1, MeOH).

Anal. Calcd for $C_{33}H_{47}N_3O_8$ (613.73): C, 64.58; H, 7.72; N, 6.85. Found: C, 64.78; H, 7.90; N, 6.80.

EXAMPLE 38

Boc-Ser(Bzl)-Ser(Bzl)-Glu(OBzl)-OH

Boc-Ser(Bzl)-Glu(OBzl)-OH.CHA (76.2 g, 124 mmol) was suspended in a mixture of 1.5 liters each of $H_2O$ and EtOAc. To this mixture, 10% $H_2SO_4$ was added until it became acidic ($\sim$pH 2.5) and the solid dissolved. The organic layer containing the dipeptide free acid was washed with $H_2O$ (2 times), dried, and evaporated to dryness leaving a clear oil (68.5 g). It was treated with 3 liters of freshly prepared 4.1 N HCl in THF for 45 minutes and evaporated to an oily residue which was re-evaporated twice more with THF. The residue (HCl.H-Ser(Bzl)-Glu(OBzl)-OH) was dissolved in DMF (500 ml), chilled to 0°, and treated with Boc-Ser(Bzl)-OSu (48.66 g, 124 mmol), followed immediately by 27 ml of Et$_3$N. The mixture was stirred overnight at 25° during which time more Et$_3$N was added occassionally in order to maintain the reaction slightly basic. Some small quantities of insoluble matters were removed by filtration and the filtrate evaporated to an oil which was taken up in EtOAc, washed with 5% HOAc (acidify with more HOAc if necessary), $H_2O$, dried over $Na_2SO_4$, and evaporated again to dryness. The product was crystallized from EtOAc with petroleum ether: yield, 71.8 g (83.7%); mp 112°–113°; $[\alpha]_D^{25}=+17.91°$ (c 1, THF).

Anal. Calcd for $C_{37}H_{45}N_3O_{10}$ (691.75): C, 64.24; H, 6.56; N, 6.07. Found: C, 64.32; H, 6.30; N, 6.19.

EXAMPLE 39

Boc-Thr(Bzl)-OSu

Boc-Thr(Bzl)-OH (23.2 g, 75 mmol) was stirred with HOSu (9.5 g, 82.5 mmol) and DCC (17.0 g, 82.5 mmol) for 3 hours. The insoluble by-product was filtered off and the filtrate evaporated to an oil which was taken up in ether (400 ml). On standing at 4° for a few hours more by-product (DCU) was formed. It was filtered off again and the filtrate evaporated to a semisolid which was crystallized from i-PrOH, to give 29.5 g (mp 70°–75°) of crude material. The crude was recrystallized from EtOH; yield, 21.2 g (69.8%); mp 104°–106°; $[\alpha]_D^{25}=+6.04°$ (c 1, CHCl$_3$); [lit. mp 94°; $[\alpha]_D^{22}=-8.5°$ (c 1, MeOH); Danho and Li, Int. J. Peptide Protein Res., 3, 81 (1971)].

Anal. Calcd for $C_{20}H_{26}N_2O_7$(406.44): C, 59.10; H, 6.44; N, 6.89. Found: C, 59.16; H, 6.52; N, 6.68.

EXAMPLE 40

Boc-Thr(Bzl)-Ser(Bzl)-Ser(Bzl)-Glu(OBzl)-OH

Boc-Ser(Bzl)-Ser(Bzl)-Glu(OBzl)-OH (71.6 g, 104 mmol) was treated with 2.7 liters of freshly prepared 3.9 N HCl in THF for 45 minutes. The mixture was evaporated to dryness and the residue evaporated twice more with THF to give a solid mass (59.3 g; mp 161°–165°). It was collected and washed with ether and stirred in 500 ml of DMF with Boc-Thr(Bzl)-OSu (38.2 g, 94 mmol) in the presence of Et$_3$N (25 ml) at 0° for 1 hour and then at 25° for 15 hours. More Et$_3$N (14.5 ml) was added in serveral portions during this time to maintain the reaction slightly basic. Some insoluble matter formed was filtered off and the filtrate evaporated to an oil which was dissolved in EtOAc (1.5 liters), washed with 5% HOAc, $H_2O$ (2 times), dried (Na$_2$SO$_4$), and evaporated to a solid mass. The product was recrystallized from EtOAc and petroleum ether to yield, 64.8 g (78.1%); mp 115°–118°; $[\alpha]_D^{25}=+11.64°$ (c 1, DMSO).

Anal. Calcd for $C_{48}H_{58}N_4O_{12}$ (882.97): C, 65.29; H, 6.62; N, 6.35. Found: C, 64.99; H, 6.77; N, 6.32.

EXAMPLE 41

Boc-Asp(OBzl)-Thr(Bzl)-Ser(Bzl)-Ser(Bzl)-Glu(OBzl)-OH

Boc-Thr(Bzl)-Ser(Bzl)-Ser(Bzl)-Glu(OBzl)-OH (54.5 g, 61.7 mmol) was treated with HCl in THF (1.5 liters; 4.1 N; 40 min) and worked up as usual to give HCl.H-Thr(Bzl)-Ser(Bzl)-Ser(Bzl)-Glu(OBzl)-OH (46.3 g, 56.6 mmol) as a white powder. It was then stirred in DMF (500 ml) with Boc-Asp(OBzl)-OSu (23.7 g, 56 mmol) at 0° for 2 hours in the presence of Et$_3$N (16 ml). The mixture was further stirred at 25° for 15 hours during which time 7.4 ml more of Et$_3$N was added. The product was worked up as usual and crystallized from CH$_2$Cl$_2$ and petroleum ether: yield, 50.35 g (82.7%); mp 111°–113°; $[\alpha]_D^{25}=+7.21°$ (c 1, DMSO).

Anal. Calcd for $C_{59}H_{69}N_5O_{15}$ (1088.22): C, 65.12; H, 6.39; N, 6.44. Found: C, 65.06; H, 6.27; N, 6.58.

EXAMPLE 42

Boc-Val-Asp(OBzl)-Thr(Bzl)-Ser(Bzl)-Ser(Bzl)-Glu(OBzl)-OH

Boc-Asp(OBzl)-Thr(Bzl)-Ser(Bzl)-Ser(Bzl)-Glu(OBzl)-OH (50.0 g, 46 mmol) was deprotected with HCl (4.15 N) in THF and worked up as usual to give 45.4 g of white solid. It was dissolved in THF (1.5 liters) and treated with ether (7 liters). On standing at 0° overnight a white solid powder was obtained (44.0 g, mp 179°–184°). Part of this material, HCl.H-Asp(OBzl)-Thr(Bzl)-Ser(Bzl)-Ser(Bzl)-Glu(OBzl)-OH (43.7 g, 42.7 mmol) was then dissolved in 500 ml of DMF, cooled to 0°, and treated with Boc-Val-OSu (15.4 g, 49 mmol) and Et$_3$N (10 ml). The mixture was stirred for 15 hours during which time more Et$_3$N (7.9 ml) was added in several portions maintaining the reaction slightly basic. The insoluble matter was removed by filtration and the filtrate evaporated to dryness. The oily residue was dissolved in CH$_2$Cl$_2$, washed with 5% HOAc, H$_2$O, dried (Na$_2$SO$_4$), and evaporated to a smaller volume (0.5 liter) when treated with petroleum ether. The product crystallized slowly during overnight standing. It was recrystallized from THF and i-PrOH to yield, 26.3 g (51.4%); mp 174°–177°; $\alpha]_D^{25}=+0.84°$ (c, 1, THF).

Anal. Calcd for $C_{64}H_{78}N_6O_{16}$ (1187.31): C, 64.74; H, 6.62; N, 7.08. Found: C, 64.60; H, 6.71; N, 6.91.

EXAMPLE 43

Boc-Val-Asp(OBzl)-Thr(Bzl)-Ser(Bzl)-Ser(Bzl)-Glu(OBzl)-HNNH$_2$

Boc-Val-Asp(OBzl)-Thr(Bzl)-Ser(Bzl)-Ser(Bzl)-Glu(OBzl)-OH (13.0 g; 10.94 mmol) was dissolved in DMF (50 ml), cooled to 0°, and treated with H$_2$NNH$_2$ (0.421 g; 13.14 mmol), HOBT (3.688 g; 24.1 mmol), and DCC (2.48 g; 12.04 mmol). NMM was then added until the reaction showed pH 7.5 (wet pH paper). The mixture was stirred for 18 hours and filtered to remove the insoluble by-products. The filtrate was evaporated to dryness and the residue treated with H$_2$O. The solid formed was collected and crystallized from DMF and i-PrOH: yield, 8.7 g (66.4%); mp 215°-218°; $[\alpha]_D^{25} = +7.62°$ (c 1, DMSO).

Anal. Calcd for $C_{64}H_{80}N_8O_{15}$ (1201.38): C, 63.98; H, 6.71; N, 9.33. Found: C 64.07; H, 6.85; N, 9.17.

EXAMPLE 44

Boc-Thr(Bzl)-Thr(Bzl)-Lys(Z)-OH

Boc-Thr(Bzl)-Lys(Z)-OH (14.0 g, 24.5 mmol) was treated with 500 ml of 4.0 N HCl in THF for 30 minutes, evaporated to dryness, and re-evaporated twice with fresh THF. The oily residue solidified when treated with ether. The dried powder (11.4 g, 21.6 mmol) of the dipeptide hydrochloride salt was then dissolved in 140 ml DMF, cooled to 0°, and treated with Boc-Thr(Bzl)-OSu (8.8 g, 21.6 mmol) followed by 3.5 ml of Et₃N. A few drops of Et₃N was added to maintain a slightly basic condition while the mixture was stirred for an additional 24 hours at 25°. It was acidified with 5 ml of HOAc and then diluted with a large volume of water. The solid crude product precipitated was collected, dissolved in EtOAc, washed with H₂O, dried over Na₂SO₄, and evaporated to dryness, leaving a glassy solid mass. Crystallized from EtOAc and petroleum ether: yield, 13.8 g (83.7%); mp 110°-112°; $[\alpha]_D^{25} = +19.45°$ (c 1, EtOAc).

Anal. Calcd for $C_{41}H_{54}N_4O_{10}$ (762.87): C, 64.55; H, 7.13; N, 7.34. Found: C, 64.41; H, 7.09; N, 7.44.

EXAMPLE 45

Boc-Ile-Thr(Bzl)-Thr(Bzl)-Lys(Z)-OH

Boc-Thr(Bzl)-Thr(Bzl)-Lys(Z)-OH (41.5 g, 54 mmol) was treated with 500 ml of freshly prepared 3.55 n HCl in THF for 25 minutes and evaporated to a syrup which was re-evaporated twice with fresh THF. The oily residue solidified when treated with ether. It was collected and washed with ether to give 37.4 g of crude hydrochloride salt of the tripeptide, dissolved in 500 ml of DMF, chilled to 0°, and treated with Boc-Ile-OSu (17.4 g, 53 mmol) followed by 16 ml of Et₃N. The mixture was stirred at 25° overnight during which time more Et₃N was added in small portions (6.2 ml total) to maintain a slightly basic condition. The resultant mixture was filtered and the filtrate evaporated to an oil which was extracted into EtOAc, washed with 5% HOAc, H₂O dried over Na₂SO₄, and evaporated to give a yellowish oil. It was crystallized from EtOAc and petroleum ether. The crude solid thus obtained (39.6 g, mp 140°-142°) was found to be contaminated with several minor impurities. The material was then rechromatographed on a silica gel 60 (70–230 mesh) column (4.7×67 cm) using CHCl₃-MeOH (95:5) as eluent. The fractions containing the desired product (monitored by tlc) were pooled and evaporated to give an oily product which was crystallized from CHCl₃ and petroleum ether: yield, 19.1 g (41.2%); mp 144°-146°; $[\alpha]_D^{25} = +2.40°$ (c 1, CHCl₃).

Anal. Calcd for $C_{47}H_{65}N_5O_{11}$ (876.06): C, 64.44; H, 7.48; N, 7.99. Found: C, 63.47; H, 7.38; N, 7.80.

EXAMPLE 46

Boc-Val-Asp(OBzl)-Thr(Bzl)-Ser(Bzl)-Ser(Bzl)-Glu(OBzl)-Ile-Thr(Bzl)-Thr(Bzl)-Lys(Z)-OH

Boc-Ile-Thr(Bzl)-Thr(Bzl)-Lys(Z)-OH (0.439 g, 0.496 mmol) was treated with 4 N HCl in THF for 30 minutes and worked up as usual to give 0.39 g of HCl.H-Ile-Thr(Bzl)-Thr(Bzl)-Lys(Z)-OH. Boc-Val-Asp(OBzl)-Thr(Bzl)-Ser(Bzl)-Ser(Bzl)-Glu(OBzl)-HNNH₂ (0.59 g, 0.492 mmol) was then dissolved in 6 ml of DMF, cooled to −25°, and treated with 0.57 ml of 4.3 N HCl in THF (2.46 mmol) followed immediately by 0.1 ml of i-amylnitrite (0.74 mmol). After stirring at −20°--25° for 30 minutes, the temperature was lowered to −35° when 0.42 ml of Et₃N and HCl.H-Ile-Thr(Bzl)-Thr(Bzl)-Lys(Z)-OH (0.39 g) prepared above were added. The mixture was stirred at −20° for 30 minutes and then at 4° for 48 hours during which time Et₃N was added from time to time in order to keep the pH at about 7.5. The reaction was then diluted with 250 ml of 5% HOAc and the solid product formed was collected and washed with H₂O, MeOH, ether, and dried over NaOH pellets in vacuo to give 0.82 g of crude material (mp 244°-254°). It was dissolved in DMSO and precipitated by addition of MeOH: yield, 0.698 g (81.7%); mp 268°-271°.

Anal. Calcd for $C_{106}H_{133}N_{11}O_{24}$ (1945.21): C, 65.46; H, 6.89; N, 7.92. Found: C, 65.32; H, 6.99; N, 8.18.

EXAMPLE 47

Ac-Ser(Bzl)-Asn-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(Z)-OH

Boc-Val-Asp(OBzl)-Thr(Bzl)-Ser(Bzl)-Ser(Bzl)-Glu(OBzl)-Ile-Thr(Bzl)-Thr(Bzl)-Lys(Z)-OH (0.698 g, 0.358 mmol) was treated with 10 ml of TFA for 30 minutes and the peptide salt was precipitated with ether. It was collected on a suction filter, washed with ether and dried to give 0.652 g of material (0.333 mmol as TFA salt). In a separate flask, Ac-Ser(Bzl)-Asn-Ala-Ala-HNNH₂ (0.17 g, 0.335 mmol) was suspended in 7 ml DMF and treated with 0.27 ml of 6.18 N HCl in THF at −20°. To the mixture, 0.68 ml of 10% i-amylnitrite in DMF was added and the solution stirred at the same temperature for 30 minutes. The temperature was lowered to −30° when 0.2344 ml of Et₃N (1.675 mmol) was added followed by the TFA salt of decapeptide (0.652 g) prepared above. The mixture was diluted with 3 ml of DMSO at −20° and adjusted to a slightly basic condition (pH 7.5 to wet pH paper) with a few drops of Et₃N. It was stirred at −20° for 30 minutes and then at 4° for 5 days. More DMSO (5 ml) and Et₃N were added during this period of time to maintain the slightly basic conditions and to keep the reaction from becoming a gel. The entire solution was then poured into 5% HOAc (250 ml) to give a white precipitate which was collected, washed with H₂O, MeOH, ether, and dried. The crude product (0.702 g; mp 290°-291°) was reprecipitated from DMSO with MeOH: yield, 0.348 g (42.0%); mp 296°-298° (d); $[\alpha]_D^{25} = +3.77°$ (c 1, DMSO).

Anal. Calcd for $C_{123}H_{153}N_{16}O_{29}$ (2319.58): C, 63.68; H, 6.65; N, 9.66. Found: C, 63.44; H, 6.83; N, 9.50.

EXAMPLE 48

Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(Z)-OH

Ac-Ser(Bzl)-Asp(OBzl)-Ala-Ala-HNNH₂ (0.408 g, 0.68 mmol) suspended in 10 ml DMF was cooled to −20° and treated with freshly prepared 5.43 N HCl in THF (0.627 ml, 3.4 mmol) followed by 10% i-amylnitrite in DMF (1.39 ml, 1.03 mmol). After stirring for 30 minutes, it was cooled down to −30° when Et₃N (0.476 ml, 3.4 mmol) was added followed by the TFA salt of the decapeptide H-Val-Asp(OBzl)-Thr(Bzl)-Ser(Bzl)-

Ser(Bzl)-Glu(OBzl)-Ile-Thr(Bzl)-Thr(Bzl)-Lys(Z)-OH (1.334 g, 0.68 mmol). The mixture was stirred at −20° for 30 minutes and then at 4° for 5 days during which time more Et$_3$N and DMSO were added in order to maintain the reaction at a slightly basic condition and to keep the gel from forming. The entire reaction was poured into 5% HOAc (300 ml) and the solid precipitate formed was collected, washed with H$_2$O, MeOH, ether, and dried to give 1.49 g of material melting at 296°–299°. The product was reprecipitated from DMSO with MeOH: yield, 1.40 g (85.37%); mp 297°–299°; $[\alpha]_D^{25} = +6.37°$ (c 1, DMSO).

Anal. Calcd for C$_{130}$H$_{158}$N$_{15}$O$_{30}$ (2410.684): C, 64.77; H, 6.61; N, 8.72. Found: C, 64.53; H, 6.73; N, 8.81.

EXAMPLE 49

Ac-Ser(Bzl)-Asp(OBzl)-Ala-Ala-Val-Asp(OBzl)-
Thr(Bzl)-Ser(Bzl)-Ser(Bzl)-Thr(Bzl)-Ile-Thr(Bzl)-
Thr(Bzl)-Lys(Z)-Asp(OBzl)-Leu-Lys(Z)-Glu(OBzl)-
Lys(Z)-Lys(Z)-Glu(OBzl)-Val-Val-Glu(OBzl)-
Glu(OBzl)-Ala-Glu(OBzl)-Asn-OBzl

The tetradecapeptide of Example 48 (1.35 g, 0.558 mmol) was stirred with HOBT . H$_2$O (0.188 g, 1.23 mmol) for a few minutes in a mixture of 15 ml each of DMF and DMSO. The mixture was then cooled in an icebath when DCC (0.126 g, 0.614 mmol) was added and the stirring continued for 24 hours at the same temperature. In a separate flask Boc-Asp(OBzl)-Leu-Lys(Z)-Glu(OBzl)-Lys(Z)-Glu(OBzl)-Val-Val-Glu(OBzl)-Glu (OBzl)-Ala-Glu(OBzl)-Asn-OBzl (4.0 g, 1.43 mmol) was treated with 40 ml of TFA for 25 min. and the TFA salt of the ensuing tetradecapeptide precipitated quickly with addition of a large volume of ether. The solid formed was collected and washed thoroughly with ether to give 3.74 g of white powder (TFA salt of C-terminal tetradecapeptide). Part of this material (1.567 g, 0.5583 mmol) was added to the active ester derived from the amino terminal tetradecapeptide as prepared above in a DMF-DMSO mixture. A few drops of NMM was added to bring the pH of the reaction to 7.5–8.0, and the stirring was continued for 1 hour at 0° and then 5 days at 25°. The reaction was then poured into 1.5l of 5% acetic acid. The precipitated product was washed thoroughly with H$_2$O, MeOH, DMF, MeOH and ether to give 2.21 g of the desired product melting above 300°.

Anal. Calcd for C$_{273}$H$_{335}$N$_{33}$O$_{63}$ (5089.69): C, 64.47; H, 6.64; N, 9.09 Found: C, 63.27; H, 6.50; N, 8.88.

Amino Acid Anal.: Asp, 3.83; Thr, 3.12; Ser, 2.81; Glu, 6.14; Ala, 3.00; Val, 2.89; Ile, 1.30; Leu, 0.77; Lys, 3.72; NH$_3$, 2.01.

EXAMPLE 50

Ac-Ser-Asp-Ala-Ala-Val-Asp-Thr-Ser-Ser-Glu-Ile-
Thr-Thr-Lys-Asp-Leu-Lys-Glu-Lys-Lys-Glu-Val-Val-
Glu-Glu-Ala-Glu-Asn [Thymosin α$_1$].

The product of Example 49 (2.21 g, 0.435 mmol) was dissolved in 8 ml of TFA, mixed with 4 ml of anisole and stirred with anhydrous HF at 0° for 30 minutes. The acids were removed at 0° (vacuum distillation) and the solid residue which remained was dissolved in 200 ml H$_2$O, washed twice with ether, evaporated to half of the volume and lyophilyzed to give 1.1 g of crude product. It was purified by passing through a Sephadex G-10 column (3×80 cm; 0.2 M HOAc) and then a DEAE-Sephadex column (3×75 cm) eluted with increasing concentrations of ammonium acetate (pH 7.0, 0.025 M 0.25 M) followed by dilute acetic acid. The fractions containing the desired material were pooled and lyophilized to give 0.281 g of amorphous white powder.

On acrinamide gel isolectrofocusing, the synthetic-material migrates identically as the natural thymosin α$_1$ isolated from bovine thymus gland (A.L. Goldstein, T.L.K. Low, C.Y. Lai and S.S. Wang, U.S. Patent Application Serial No. 766,638, Feb. 8, 1977; A.L. Goldstein et al., Proc. Natl. Acad. Sci. (U.S.A.), 74, 725 (1977)).

Amino Acid Anal.: Asp, 3.86; Thr, 3.22; Ser, 3.05; Glu, 6.[3; Ala, 3.]5; Val, 3.04; Ile, 1.12; Leu, 0.94; Lys, 3.88; NH$_3$, 2.25.

EXAMPLE 51

Ac-Ser(Bzl)-Asn-Ala-Ala-Val-Asp(OBzl)-Thr(Bzl)-
Ser(Bzl)-Ser(Bzl)-Glu(OBzl)-Ile-Thr
(Bzl)-Thr(Bzl)-Lys(Z)-Asp(OBzl)-Leu-Lys(Z)-
Glu(OBzl)-Lys(Z)-Lys(Z)-Glu(OBzl)-Val
-Val-Glu(OBzl)-Glu(OBzl)-Ala-Glu(OBzl)-Asn-OBzl.

The product of Example 47 (0.866 g, 0.373 mmol) was stirred with HOBT . H$_2$O (0.126 g, 0.82 mmol) in a mixture of DMSO (8 ml) and DMF (6 ml) and chilled in an icebath. The mixture was treated with DCC (0.085 g, 0.411 mmol) and then stirred at 0° for 24 hours. It was then mixed with the TFA salt of the C-terminal tetradecapeptide prepared as in Example 49 (1.05 g, 0.373 mmol) and 2 ml more of DMSO. A few drops of NMM were added to bring the pH to 7.5–8.0 and the stirring was continued at 0° for 1 hour and then at 25° for 5 days. Worked up as mentioned above in Example 49 gave 1.5775 g of fully protected octacosapeptide.

Anal. Calcd. for C$_{266}$H$_{330}$N$_{34}$O$_{62}$ (4995.51): C, 63.95; H, 6.66; N, 9.53 Found: C, 63.20; H, 6.60; N, 9.49.

Amino Acid Anal. Asp, 3.96; Thr, 2.87; Ser, 2.46; Glu, 6.03; Ala, 3.05; Val, 3.00; Ile, 1.04; Leu, 0.76; Lys, 3.91; NH$_3$, 4.45.

EXAMPLE 52

Ac-Ser-Asn-Ala-Ala-Val-Asp-Thr-Ser-Ser-Glu-Ile-
Thr-Thr-Lys-Asp-Leu-Lys-Blu-Lys
-Lys-Glu-Val-Val-Glu-Glu-Ala-Glu-Asn
[(Asn$^2$)-Thymosin α$_1$].

The compound of Example 51 (1.5775 g, 0.3157 mmol) was dissolved in 10 ml of TFA which contained 3 ml of anisole. The mixture was stirred with 45 ml of HF at 0° for 30 min and then worked up as described for Example 50. Purification on Sephadex G-10 and DEAE-sephadex columns as described above gave 0.283 g of white amorphous product. The compound migrated at the position slightly less acidic than natural thymosin α$_1$ on acrinamide gel isoelectrofocusing in agreement with difference in the structure.

Amino Acid Anal. Asp, 3.89; Thr, 3.00; Ser, 2.93; Glu, 5.68; Ala, 3.02; Val, 2.63; Ile, 1.12; Leu, 0.86; Lys, 4.03.

EXAMPLE 53

Boc-Glu(OBzl)-Lys(Z)-Lys(Z)-HNNH$_2$

Boc-Glu(OBzl)-Lys(Z)-Lys(Z)-OH (43.2 g, 50 mmol) was treated in DMF (280 ml) at 0° with H$_2$NNH$_2$ (1.76 ml, 55 mmol) and HOBT . H$_2$O (15.3 g, 100 mmol) followed by DCC (11.33 g, 55 mmol). The mixture was stirred at 0° for 2 hours and then at 25° overnight during which time some NMM was added to maintain the reaction slightly basic. On evaporation of the solvents, the oily residue remained was treated with a large volume of water which turned the crude product into a solid mass. It was collected was washed with H₂O, i-PrOH and ether. The powder obtained was crystallized twice from i-PrOH: yield, 31.93 g (73.0%); mp 164°-169°; $[\alpha]_D^{25} = 1.37°$ (c 1, THF).

Anal. Calcd for $C_{45}H_{61}N_7O_{11}$ (875.99): C, 61.69; H, 7.02; N, 11.19. Found: C, 61.86; H, 7.06; N, 10.93.

EXAMPLE 54

Boc-Asp(OBzl)-Leu-Lys(Z)-HNNH₂

Boc-Asp(OBzl)-Leu-Lys(Z)-OH (14.8 g, 21.0 mmol) was treated in DMF (80 ml) at 0° with H₂NNH₂ (0.80 ml, 25.0 mmol), HOBT . H₂O (7.1 g, 46.2 mmol), and DCC (4.7 g, 23.0 mmol). The mixture was stirred at 0° (2 hours) and then at 25° (17 hours). Work-up as the above compound gave 9.2 g (61.5%) of the desired product: mp 133°-137°; $[\alpha]_D^{25} = -19.36°$ (c 1, THF).

Anal. Calcd for $C_{36}H_{52}N_6O_9$ (712.82): C, 60.65; H, 7.35; N, 11.79. Found: C, 60.80; H, 7.42; N, 11.51.

EXAMPLE 55

Nα-Boc-α-benzyl-L-aspartyl benzhydrylamine resin.

Benzhydrylamine resin (5 g, Beckman Lot No. 00658; N, 0.52%, 0.371 mmol/g) was stirred with 125 ml of 25% Et₃N in CH₂Cl₂ for 10 min and then washed a few times with fresh CH₂Cl₂. It was then suspended in 120 ml of CH₂Cl₂ and stirred with Nα-Boc-α-benzyl-L-aspartic acid (1.62 g, 5.0 m mol) and DCC (1.03 g, 5.0 m mol) for 17 hr. The amino acylated resin was collected, washed thoroughly with CH₂ Cl₂, DMF and MeOH. After drying, the resin was benzoylated with 1.5 ml pyridine and 1.65 ml benzoyl chloride in 55 ml of CH₂Cl₂ for 15 min at 0°. The resin was washed with CH₂Cl₂, MeOH to give 5.35 g of desired material. Amino acid analysis indicated that there was 0.296 m mol/g of aspartic acid.

EXAMPLE 56

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn (Thymosin α₁).

Nα-Boc-α-benzyl-L-aspartyl benzhydrylamine resin (2.5 g, 0.74 m mol) was placed in the reaction vessel of an automatic solid phase peptide synthesis apparatus which was programmed to perform the following steps (40 ml solvent or reagents, unless otherwise stated) in each cycle:

(1) three washings with CH₂Cl₂,
(2) prewash with 33% TFA in CH₂Cl₂,
(3) stir 25 min with 33% TFA in CH₂Cl₂,
(4) three washings with CH₂Cl₂,
(5) prewash with 10% Et₃N in CH₂ Cl₂,
(6) stir 10 min with 10% Et₃N in CH₂Cl₂,
(7) three washings each with CH₂Cl₂, i-PrOH, CH₂Cl₂,
(8) stir 120 min with 2.22 m mol each of Boc-Glu(OBzl)-OH and DCC in CH₂Cl₂,
(9) three washings each with CH₂Cl₂, DMF, i-PrOH, CH₂Cl₂,
(10) stir 10 min with 10% Et₃N,
(11) three washings with CH₂Cl₂,
(12) stir 120 min with 1.11 m mol each of Boc-Glu(OBzl)-OH and DCC in CH₂Cl₂,
(13) three washings each with CH₂Cl₂, DMF, i-PrOH.

The synthetic cycle was repeated using the following amino acids, sequentially, one at a time in step 8 and step 12:

Boc-Ala-OH, Boc-Glu(OBzl)-OH, Boc-Glu(OBzl)-OH, Boc-Val-OH, Boc-Val-OH,
Boc-Glu(OBzl)-OH, Boc-Lys(Cl₂Z)-OH, Boc-Lys(Cl₂Z)-OH, Boc-Glu(OBzl)-OH,
Boc-Lys(Cl₂Z)-OH, Boc-Leu-OH, Boc-Asp(OBzl)-OH, Boc-Lys(Cl₂Z)-OH, Boc-Thr(Bzl)-OH, Boc-Thr(Bzl)-OH, Boc-Ile-OH, Boc-Glu(OBzl)-OH, Boc-Ser(Bzl)-OH,
Boc-Ser(Bzl)-OH, Boc-Thr(Bzl)-OH, Boc-Asp(OBzl)-OH, Boc-Val-OH, Boc-Ala-OH,
Boc-Ala-OH, Boc-Asp(OBzl)-OH, Boc-Ser(Bzl)-OH, and CH₃COOH.

On completion of the automated synthetic cycles, 4.15 g of protected peptide resin was obtained. Part of this material (0.91 g) was then treated with 10 ml of anhydrous HF in the presence of 1 ml of anisole at 0° for 60 min. After evaporation of the acid (in vacuo, 0°), the residue was extracted with 5 ml of TFA, diluted with water, washed several times with ether, evaporated to smaller volume and desalted on a Sephadex G-10 column (2.5×60 cm). The fractions containing the material (absorption at 215 mm) were pooled and lyophilized to give 127 mg of crude product. It was then chromatographed on a DEAE-Sephadex A-25 column (1.5×70 cm) using a linear gradient made up from 1 L each of 0.05 m Tris-Hcl (pH8.0) with and without 0.3 M NaCl. The main peak was pooled, desalted on the Sephadex G-10 column (0.2M HOAc) and lyophilized to give 34 mg of product migrating identically with the natural thymosin α₁ and also with the synthetic thymosin α₁ prepared by the conventional process. The overall yield is calculated to be 6.74% based on the aspartic acid content of the Nα-Boc-α-benzyl-L-aspartyl benzhydrylamine resin. Amino acid composition of the product is Asp, 4.10; Thr, 2.78; Ser, 3.22; Glu, 6.43; Ala, 262; Val, 1.66; Ile, 0.79; Leu, 0.91; Lys, 4.15 (24 hr hydrolysis in 4 N methane sulfonic acid, 110°).

I claim:

1. Ac-Ser($R^1$)-Asp($OR^2$)-Ala-Ala-Val-Asp($OR^2$)-Thr($R^3$)-Ser($R^1$)-Ser($R^1$)-Glu($OR^4$)-Ile-Thr($R^3$)-Thr($R^3$)-Lys($R^5$)-Asp($OR^2$)-Leu-Lys($R^5$)-Glu($OR^4$)-Lys($R^5$)-Lys($R^5$)-Glu($OR^4$)-Val-Val-Glu($OR^4$)-Glu($OR^4$)-Ala-Glu($OR^4$)-Asn-$OR^6$ wherein Ac is acetyl; $R^1$ is a conventional protecting group for the hydroxyl group of the serine residue; $R^2$ is a conventional carboxyl protecting group; $R^3$ is a conventional protecting group for the hydroxyl group of threonine; $R^4$ is a conventional carboxyl protecting group; $R^5$ is a conventional ω-amino protecting group; and $R^6$ is a conventional carboxyl protecting group.

2. The compound of claim 1 wherein $R^1$ is benzyl, $R^2$ is benzyl, $R^3$ is benzyl, $R^4$ is benzyl, $R^5$ is benzyloxycarbonyl and $R^6$ is benzyl.

3. Ac-Ser-Asp-Ala-Ala-Val-Asp-Thr-Ser-Ser-Glu-Ile-Thr-Thr-Lys and pharmaceutically acceptable salts thereof.

4. Asp-Leu-Lys-Glu-Lys-Lys-Glu-Val-Val-Glu-Glu-Ala-Glu-Asn and pharmaceutically acceptable salts thereof.

5. Glu-Lys-Lys-Glu-Val-Val-Glu-Glu-Ala-Glu-Asn and pharmaceutically acceptable salts thereof.

6. Glu-Val-Val-Glu-Glu-Ala-Glu-Asn and pharmaceutically acceptable salts thereof.

7. H-Asp(OBzl)-Leu-Lys(Z)-Glu(OBzl)-Lys(Z)-Lys(Z)-Glu(OBzl)-Val-Val-Glu(OBzl)-Glu(OBzl)-Ala-

Glu(OBzl)-Asn-OBzl and the trifluoroacetic acid salt thereof, wherein Bzl is benzyl and Z is benzyloxycarbonyl.

8. Ac-Ser(Bzl)-Asp(OBzl)-Ala-Ala-Val-Asp(OBzl)-Thr(Bzl)-Ser(Bzl)-Ser(Bzl)-Glu-(OBzl)-Ile-Thr(Bzl)-Thr(Bzl)-Lys(Z)-OH wherein Ac is acetyl, Bzl is benzyl and Z is benzyloxycarbonyl.

9. Ac-Ser($R^1$)-Asp($OR^2$)-Ala-Ala-Val($OR^2$)-Asp($OR^2$)-Thr($R^3$)-Ser($R^1$)-Ser($R^1$)-Glu($OR^4$)-Ile-Thr($R^3$)-Thr($R^3$)-Lys($R^5$)-Asp($OR^2$)-Leu-Lys($R^5$)-Glu($OR^4$)-Lys($R^5$)-Lys($R^5$)-Glu($OR^4$)-Val-Val-Glu($OR^4$)-Glu($OR^4$)-Ala-Glu($OR^4$)-Asp-(CONH-CH($C_6H_5$)-  Resin)-$OR^2$ wherein Ac is acetyl; $R^1$ is a conventional protecting group for the hydroxyl group of the serine residue; $R^2$ is a conventional carboxyl protecting group; $R^3$ is a conventional protecting group for the hydroxyl group of threonine; $R^4$ is a conventional carboxyl protecting group; $R^5$ is a conventional ω-amino protecting group and $R^6$ is a conventional carboxyl protecting group.

10. The compound of claim 9 wherein $R^1$ is benzyl, $R^2$ is benzyl, $R^3$ is benzyl, $R^4$ is benzyl, $R^5$ is 2,4-dichlorobenzyloxycarbonyl and $R^6$ is benzyl.

* * * * *